(12) United States Patent
Twiss et al.

(10) Patent No.: US 11,382,947 B2
(45) Date of Patent: *Jul. 12, 2022

(54) TARGETING G3BP PROTEINS TO ACCELERATE NERVE REGENERATION

(71) Applicant: University of South Carolina, Columbia, SC (US)

(72) Inventors: Jeffery L. Twiss, Columbia, SC (US); Pabitra Sahoo, West Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/857,636

(22) Filed: Apr. 24, 2020

(65) Prior Publication Data
US 2020/0360467 A1    Nov. 19, 2020

Related U.S. Application Data

(63) Continuation of application No. 15/897,444, filed on Feb. 15, 2018, now Pat. No. 10,668,128.

(60) Provisional application No. 62/459,095, filed on Feb. 15, 2017.

(51) Int. Cl.
*A61K 38/10*    (2006.01)

(52) U.S. Cl.
CPC .................................... *A61K 38/10* (2013.01)

(58) Field of Classification Search
None
See application file for complete search history.

(56) References Cited

U.S. PATENT DOCUMENTS

| 10,668,128 B2 * | 6/2020 | Twiss | A61K 38/10 |
| 2018/0250356 A1 * | 9/2018 | Twiss | A61K 38/10 |

OTHER PUBLICATIONS

Vanderweyde et al., Contrasting Pathology of the Stress Granule Proteins TIA-1 and G3BP in Tauopathies, Jun. 13, 2012, • The Journal of Neuroscience 32(24):8270-8283 (Year: 2012).*

Sahoo, Pabitra K., et al., Axonal G3BP1 Stress Granule Protein Limits Axonal mRNA Translation and Nerve Regeneration, www.nature.com/naturecommunication, 2018.

White, James P., et al., Inhibition of Cytoplasmic mRNA Stress Granule Formation by a Viral Proteinase, Cell Host & Microbe 2:295-305, 2007, Elsevier, Inc.

* cited by examiner

*Primary Examiner* — Adam Weidner
(74) *Attorney, Agent, or Firm* — Burr & Forman, LLP; Douglas L. Lineberry

(57) ABSTRACT

Methods for using a peptide to effectively increase axon growth in both naive and injury-conditioned neurons.

10 Claims, 53 Drawing Sheets

Specification includes a Sequence Listing.

| SG Marker colocalization (Pearson's coefficient) | |
|---|---|
| G3BP1 vs. FXR1 | 0.19 ± 0.017 |
| G3BP1 vs. FMRP | 0.27 ± 0.021 |
| G3BP1 vs. HuR | 0.23 ± 0.016 |
| FXR1 vs. FMRP | 0.19 ± 0.014 |
| FXR1 vs. HuR | 0.42 ± 0.024 |
| FMRP vs. HuR | 0.22 ± 0.017 |

| PB Marker colocalization (Pearson's coefficient) | |
|---|---|
| G3BP1 vs. DCP1A | 0.15 ± 0.011 |
| G3BP1 vs. XRN1 | 0.11 ± 0.011 |
| DCP1A vs. XRN1 | 0.29 ± 0.013 |

FIGURE 8C

|  | Total axon length (μm) | Longest axon (μm) | Axons/ neuron |
|---|---|---|---|
| GFP | 3522 ± 259 | 649 ± 36 | 7.2 ± 0.32 |
| G3BP1-GFP (ABCD domain-GFP) | 3993 ± 322 [NS] | 745 ± 46 [$p \leq 0.005$] | 6.22 ± 0.28 [$p \leq 0.05$] |
| A domain-GFP | 4573 ± 329 [$p \leq 0.05$] | 801 ± 44 [$p \leq 0.01$] | 7.2 ± 0.31 [NS] |
| B domain-GFP | 6396 ± 726 [$p \leq 0.0005$] | 1031 ± 55 [$p \leq 0.0001$] | 6.1 ± 0.30 [$p \leq 0.05$] |
| C domain-GFP | 3893 ± 315 [NS] | 792 ± 40 [$p \leq 0.01$] | 7.1 ± 0.31 [NS] |
| D domain-GFP | 2329 ± 219 [$p \leq 0.001$] | 456 ± 35 [$p \leq 0.0005$] | 7.3 ± 0.38 [NS] |
| CD domain-GFP | 2144 ± 165 [$p \leq 0.0001$] | 517 ± 27 [$p \leq 0.005$] | 6.0 ± 0.28 [$p \leq 0.01$] |
| BCD domain-GFP | 5675 ± 327 [$p \leq 0.0001$] | 910 ± 48 [$p \leq 0.0001$] | 7.2 ± 0.42 [NS] |

SEQUENCE LISTING

<160> NUMBER OF SEQ ID NOS: 4

<210> SEQ ID NO 1
<211> LENGTH: 19
<212> TYPE: PRT
<213> ORGANISM: Rattus norvegicus

<400> SEQUENCE: 1

Val Val Glu Pro Glu Pro Glu Pro Glu Pro Glu Pro Glu Pro Glu Pro
1               5                   10                  15

Val Ser Asp

<210> SEQ ID NO 2
<211> LENGTH: 19
<212> TYPE: PRT
<213> ORGANISM: Homo sapiens

<400> SEQUENCE: 2

Val Ala Glu Pro Glu Pro Asp Pro Glu Pro Glu Pro Glu Gln Glu Pro
1               5                   10                  15

Val Ser Glu

<210> SEQ ID NO 3
<211> LENGTH: 31

```
<212> TYPE: PRT
<213> ORGANISM: Rattus norvegicus

<400> SEQUENCE: 3

Tyr Gly Asn Lys Lys Asn Asn Asn Gln Asn Asn Asn Val Val Glu Pro
1               5                   10                  15
Glu Pro Glu Pro Glu Pro Glu Pro Glu Pro Glu Pro Val Ser Asp
            20                  25                  30

<210> SEQ ID NO 4
<211> LENGTH: 33
<212> TYPE: PRT
<213> ORGANISM: Homo sapiens

<400> SEQUENCE: 4

Tyr Gly Asn Lys Lys Asn Asn Asn Gln Asn Asn Asn Val Val Val Ala
1               5                   10                  15
Glu Pro Glu Pro Asp Pro Glu Pro Glu Pro Glu Gln Glu Pro Val Ser
            20                  25                  30
Glu
```

TARGETING G3BP PROTEINS TO ACCELERATE NERVE REGENERATION

This invention was made with government support under W81XWH-2013-1-308; OR120042 awarded by the Department of Defense and R01-NS041596 awarded by the National Institute of Health. The government has certain rights in the invention.

BACKGROUND OF THE INVENTION

1) Field of the Invention

The present invention relates to vehicles and methods for improving nerve regeneration after nerve injury.

2) Description of Related Art

"Peripheral nerve" is a term used synonymously to describe the peripheral nervous system. The peripheral nervous system is a network of motor and sensory nerves that connect the brain and spinal cord (the central nervous system or CNS) to the entire human body. These nerves control the functions of sensation, movement and motor coordination. The peripheral nerves are a complicated, extensive network of nerves that are the tool for the brain and spinal cord to communicate with the rest of the body. They are fragile and can be damaged easily. Trauma, including battlefield injuries, is a major cause of peripheral nerve injury along with birth trauma (brachial plexus injury) and injuries related to surgeries. Limited data is available to determine the incidence of peripheral nerve injury.

Neurons, nerve cells that are the basic building block of the nervous system, generate their own proteins within cytoplasmic processes that extend for centimeters in rodents and more than a meter in humans. These locally generated proteins are needed for regeneration after nerve injury. Protein synthesis in axons contributes to axon growth during development and regeneration.

The stress response in eukaryotic cells often inhibits translation initiation and leads to the formation of cytoplasmic RNA-protein complexes referred to as stress granules. Stress granules, dense aggregations in the cytosol (the aqueous component of the cytoplasm of a cell) comprised of proteins and RNAs, are used to store mRNAs during periods of cellular stress, but nerve injury with compromise of axon integrity paradoxically causes stress granules to disaggregate presumably releasing mRNAs for translation. Stress granules contain non-translating mRNAs, translation initiation components, and many additional proteins affecting mRNA function. Stress granules have been proposed to affect mRNA translation and stability, as well as being linked to apoptosis and nuclear processes. Stress granules also interact with P-bodies, another cytoplasmic RNP granule containing non-translating mRNA, translation repressors and some mRNA degradation machinery. Together, stress granules and P-bodies reveal a dynamic cycle of distinct biochemical and mRNA-protein complexes (mRNPs) in the cytosol, with implications for the control of mRNA function.

Nerve regeneration is abysmally slow in the peripheral nervous system and does not occur spontaneously in the central nervous system. Despite that regeneration occurs in the periphery, the slow growth in humans means that by the time regeneration occurs the distal nerve is no longer a growth-supportive environment and the target tissues are no longer receptive for reinnervation that restores the nerve supply to a part of the body. There is a pressing clinical need for treatments that will accelerate axon regeneration in peripheral nerves.

Regeneration in the brain and spinal cord is thought to fail because of extrinsic inhibitors of axon growth and the low intrinsic growth potential of central nervous system neurons. Some approaches to increase intrinsic growth potential of neurons have been shown to also overcome the extrinsic growth inhibitors. There is a pressing clinical need for better agents to increase intrinsic growth that directly target the axons.

Current products in use clinically consist of a myriad of 'gap bridging' approaches for peripheral nerve treatments. Experimentally, these have been encapsulated with various growth promoting agents (e.g., growth factors), but none have specifically targeted regeneration rates. Other approaches include exercise, which is used clinically for rehabilitation/physical therapy, but likely has some regenerative effects. For both stroke and spinal cord injury, rehabilitation is similarly used in clinics. Experimental evidence points to some enhanced regeneration with these techniques.

Accordingly, it is an object of the present invention to provide vehicles and methods for improving nerve regeneration after nerve injury.

SUMMARY OF THE INVENTION

In a first embodiment, a method for treating nerve injury in a mammal is provided. The method may include introducing a polypeptide comprising between 15 and 20 amino acids to a nerve injury site in the mammal. The polypeptide may interfere with function of stress granules and increases intra-axonal rates of translation of proteins needed for nerve regeneration. Further, the polypeptide may be an amino acid sequence set as forth in SEQ ID NO. 2. Still further, the polypeptide specifically may target mRNA storage sites in neurons and increases rates of neuron regeneration. Even further, the polypeptide may disrupt G3BP function. Further yet, disruption of G3BP functions may include activating intra-axonal mRNA translation, increasing axon growth in neurons, and accelerating nerve regeneration in vivo. Furthermore, disruption of G3BP functions may be accomplished via siRNA-mediated knockdown of G3BP1. Further yet still, disrupting G3BP1's function in an assembly of axonal stress granule structures may increase intra-axonal protein synthesis and accelerate peripheral nervous system axon regeneration. Even still further, accelerated axon growth regeneration may be facilitated by sequestering Impβ1 mRNA from translation.

In an alternative embodiment, a method of disrupting G3BP functions is provided. The method may include overexpressing a dominant-negative protein. The dominant-negative protein may: disassemble axonal stress granule-like structures, activate intra-axonal mRNA translation, increase axon growth in neurons; and accelerate nerve regeneration in vivo. Further, the protein may comprise between 15 and 20 amino acids. Still yet, the protein may have an amino acid sequence as set forth in SEQ ID NO. 2. Further still, the protein may be cell permeable and target mRNA storage sites in neurons. Yet further, disruption of G3BP functions may be accomplished via siRNA-mediated knockdown of G3BP1. Further yet still, disrupting G3BP1's function in an assembly of axonal stress granule structures may increase intra-axonal protein synthesis and accelerate peripheral nervous system axon regeneration. Still furthermore, preventing stress granule-like aggregation of axonal proteins during regeneration may increase the rate of axon regrowth.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 8C also shows single optical planes for axons of naïve DRG cultures.

FIG. 15A shows axon growth parameters for DRG neurons transfected as in FIG. 11B.

Figure 1:
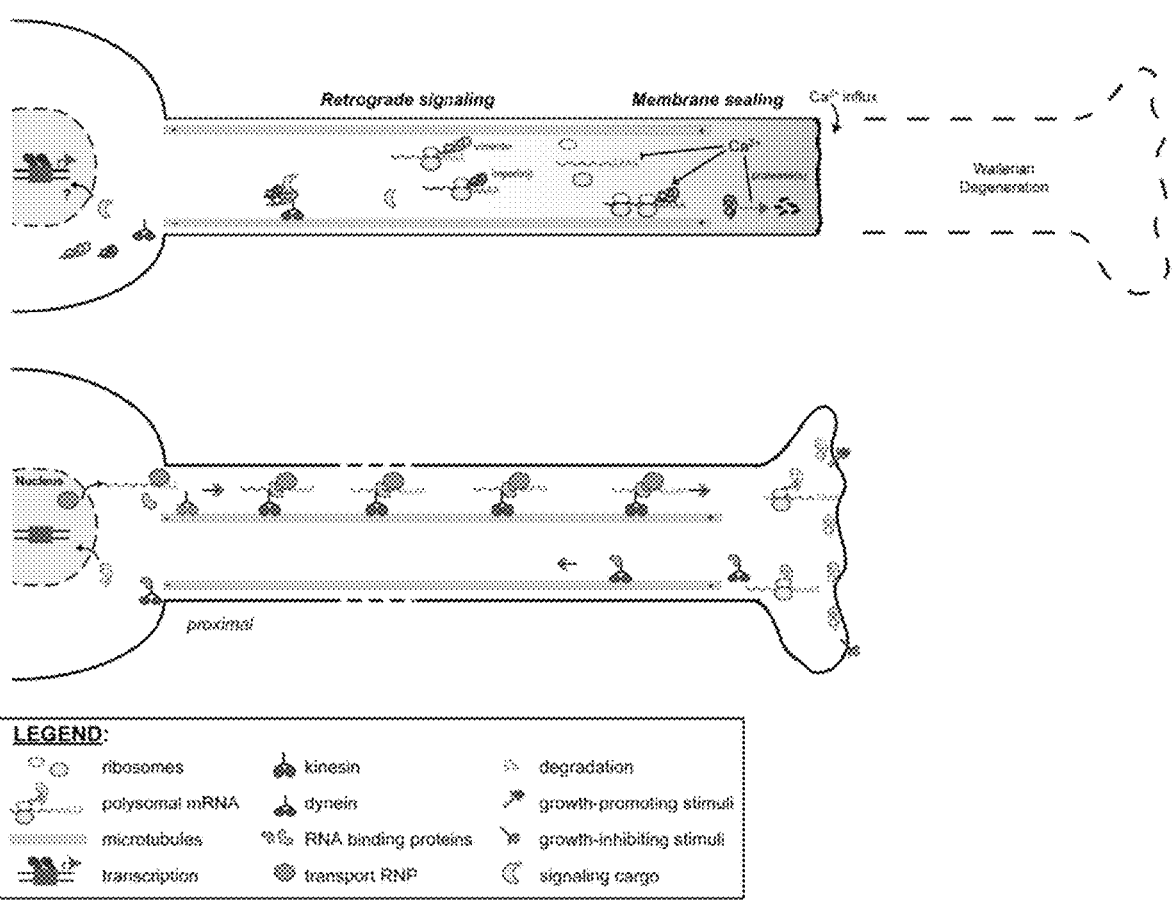
FIG. 1 shows a schematic of how translation is regulated in axons.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

As there are no currently available treatments to accelerate nerve 'regeneration'. The approach used by the current disclosure targets protein synthesis in the distal axon, the compartment of the neuron that needs to regenerate to restore function. Consequently, this provides a unique way to increase intrinsic growth potential of the neuron.

The current disclosure presents data on the general mechanism for targeting the G3BP proteins and efficacy of viral targeting for accelerating axon regeneration. In one embodiment, a cell permeable G3BP1 peptide is disclosed that may have potential for pharmaceutical development. In one particular embodiment, a method is provided for a mechanism for targeting G3BP1 function is provided.

The current disclosure provides that knockdown of G3BP1, a stress granule aggregating protein, increases axon growth in vitro. Introduction of the B domain of G3BP1 (which may include but is not limited to amino acids 140-208) and may increase axon regeneration in vitro and in vivo. Importantly, this may accelerate the rate of regeneration in vivo after peripheral nerve injury. The G3BP1 B domain is highly conserved across species.

The current disclosure discloses cell permeable peptides to conserved subregions of the G3BP1 B domain. In one embodiment, a polypeptide comprising amino acids 190-208 of rat G3BP1 increases axonal outgrowth in cultured mammalian sensory and cortical neurons and even accelerates axon growth beyond the effect of injury-conditioned sensory neurons. Structure predictions of the 190-208 G3BP1 peptide show that acidic glutamate side chains of seven glutamate-proline repeats may be arrayed along the periphery of the peptide and only conservative changes in amino acid sequence between rat, mouse and human (e.g., substitution of aspartate for glutamate). mRNA colocalization with endogenous G3BP1 protein and translation assays strongly suggest that the peptide interferes with function of stress granules and increases intra-axonal rates of translation of proteins needed for regeneration.

The current disclosures provides a cell-permeable polypeptide that specifically targets mRNA storage sites in neurons and increases rates of regeneration after traumatic injury. This may be used as the basis for therapeutic development or could increase efficacy of existing therapies. Additionally, there could be neuroprotective applications for neuropathic conditions (diabetic neuropathy, chemotherapy induced neuropathy, etc.) that have much higher incidence.

FIG. 1 shows a schematic of how translation is regulated in axons. Changes in intra-axonal translation occur after injury of peripheral nerves. mRNAs are stored before injury, and an influx of calcium recruits mRNAs into translation. Based on localization to axons and dynamic changes after injury, it is believed that 'stress granules' are the site of mRNA storage before injury and likely provide a level of mRNA sequestration after injury/during regeneration.

Figure 2:
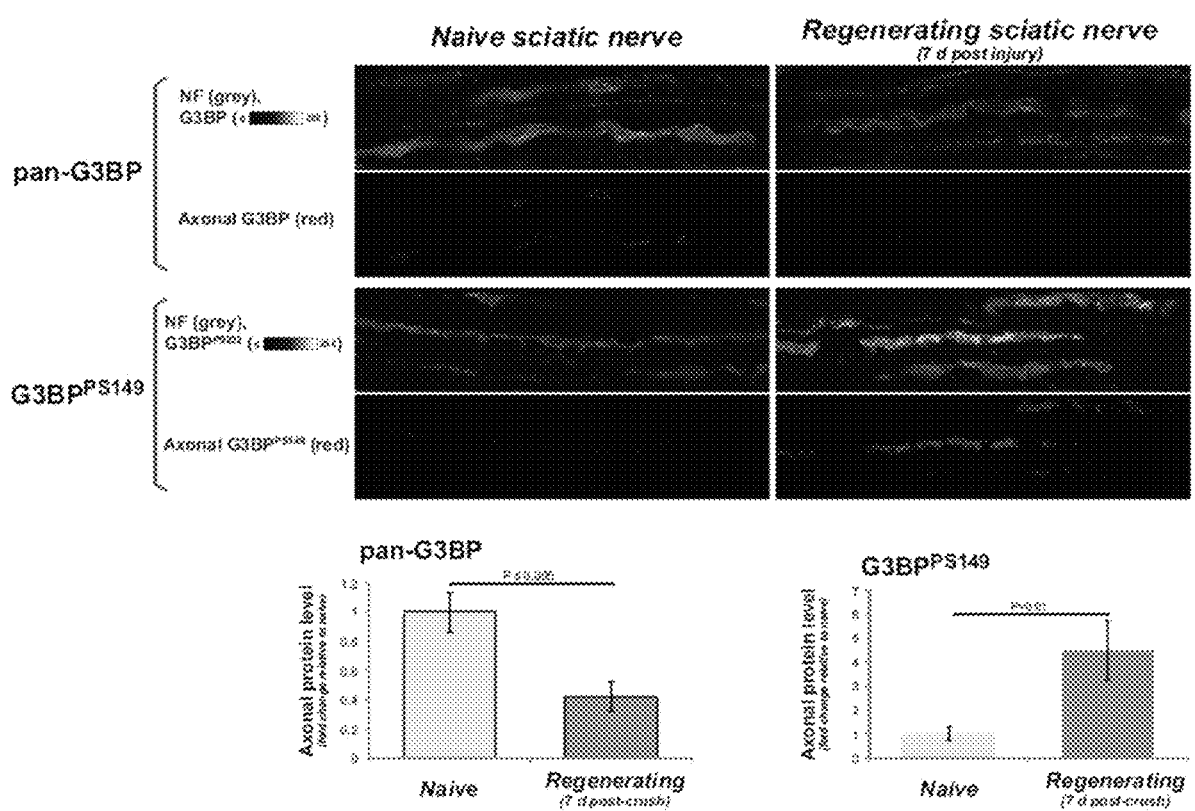
FIG. 2 shows an immunofluorescence comparison of the presence of G3BP1 protein in axons pre-injury and post-injury.

FIG. 2 illustrates that immunofluorescence shows G3BP1 protein in axons in a granular profile before injury. Seven (7) days after injury, when axons have fully initiated regeneration, granular profiles of G3BP1 in axons are decreased compared to the naive nerve. There is a commensurate increase in G3BP1 phosphorylated on serine 149. This phosphorylation is known to 'dissaggregate' G3BP1.

Figure 3:
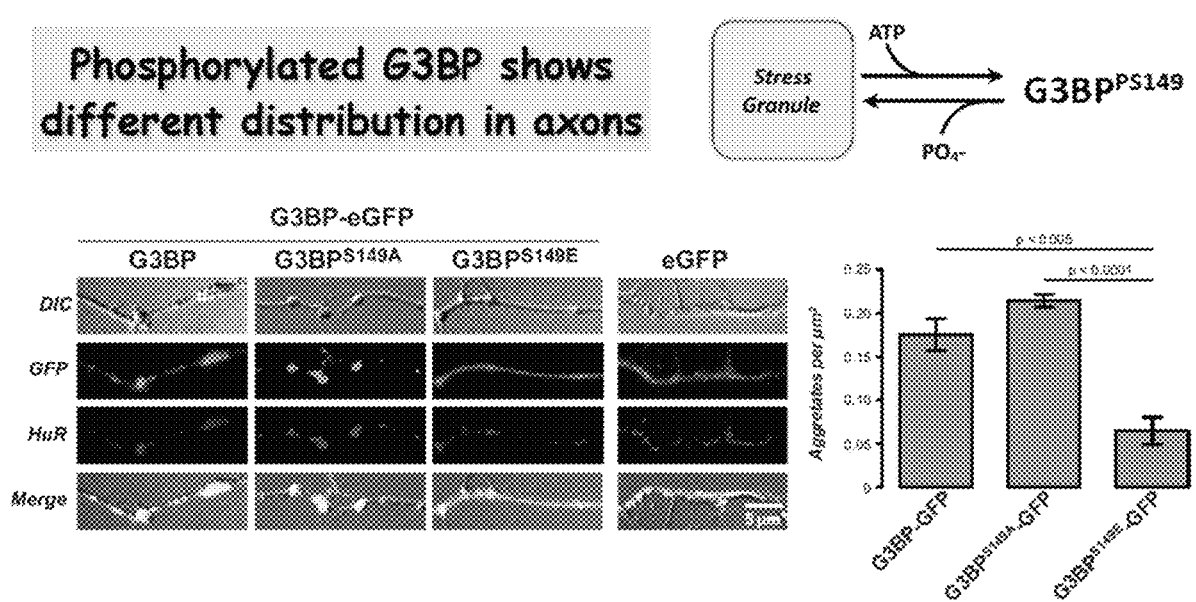
FIG. 3 shows an immunofluorescence (IF) comparison and a graph illustrating the differences in phosphorylated G3BP in axons.

FIG. 3 shows that consistent with phosphorylation decreasing G3BP1 aggregation, phosphomimetic G3BP1 (G3BP1-S149E) shows much lower aggregation in axons than does non-phosphorylatable G3BP1 (G3BP1-S149A) and wild-type G3BP1 in axons of in cultured rat sensory neurons.

Figure 4:
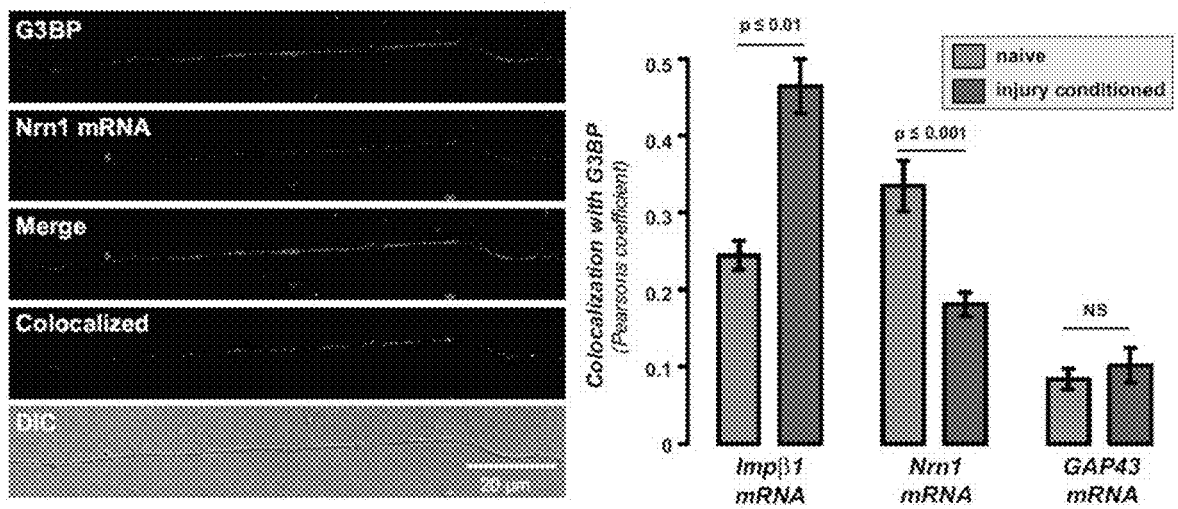
FIG. 4 shows an immunofluorescence comparison and a graph of differential colocalization of G3BP with axonal mRNAs in axons of naïve vs. injury-conditioned neurons.

FIG. 4 illustrates differential colocalization of G3BP1 with axonal mRNAs in axons of naïve vs. injury-conditioned neurons. G3BP1 colocalizes with some axonal mRNAs. Representative fluorescence in situ hybridization to detect axonal mRNA combined with antibody staining for G3BP1 protein is shown on left. Quantifications of the colocalization coefficients are shown in the graph. This comparison is for naive vs. injury-conditioned sensory neurons, where the conditioning injury triggers a rapid outgrowth of axons. Importin β1 mRNA (Impβ1), encoded by an 'injury response gene', shows increased colocalization with G3BP1 in axons of the injury-conditioned neurons. On the other hand, Neuritin 1 mRNA (Nrn1), encoded by a 'regeneration-associated gene', shows decreased colocalization with G3BP1 protein in axons of the injury-conditioned neurons. GAP43 shows low colocalization coefficients and no change with injury-conditioning.

Figure 5:
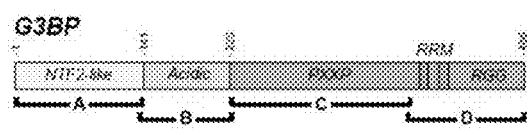
FIG. 5 shows an immunofluorescence comparison and a graph showing expression of known G3BP domains vis-à-vis axon growth.
Figure 5:
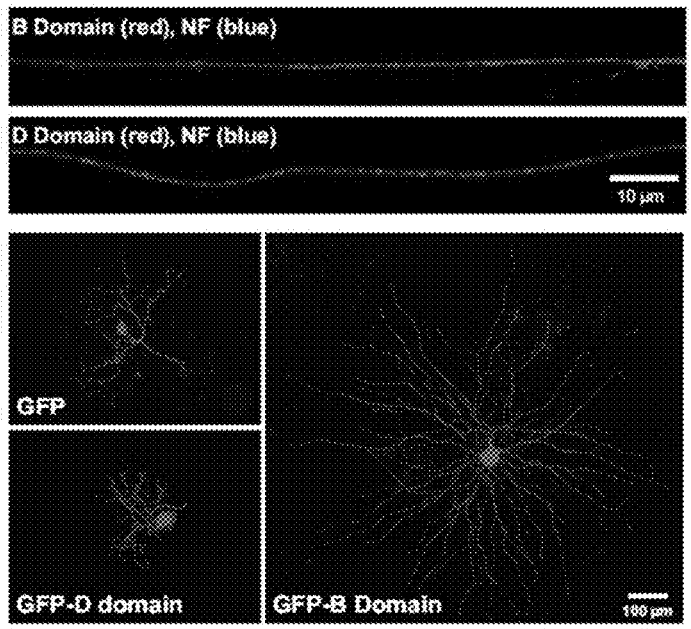
Figure 5:
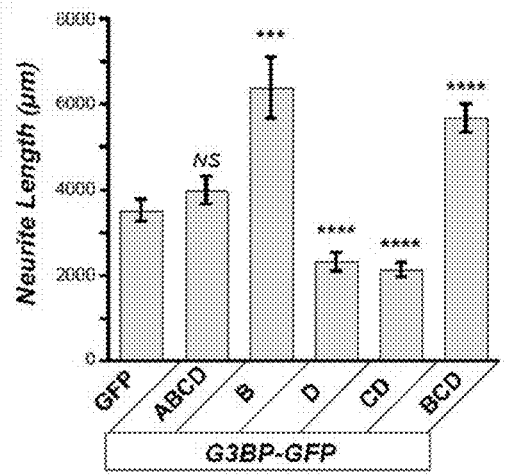

FIG. 5 shows that expression of G3BP1 domains alters axon growth. Introduction of full length (ABCD) or separate domains of G3BP1 into DRG neurons alters axon growth in culture (schematic in upper right). Representative images of B and D domain GFP fusion proteins show localization into distal axons (longitudinal images in mid-left); all other fusion proteins similarly localized into axons. Representative images of axonal outgrowth are shown on bottom left. D domain decreases axon length and B domain substantially increases axon lengths. Quantification of axonal lengths over biological replicate experiments (≥3) is shown on right (* p≤0.001, ** p≤0.0001 by a Anova with Tukey HSD post-hoc test compared to GFP control).

Figure 6:
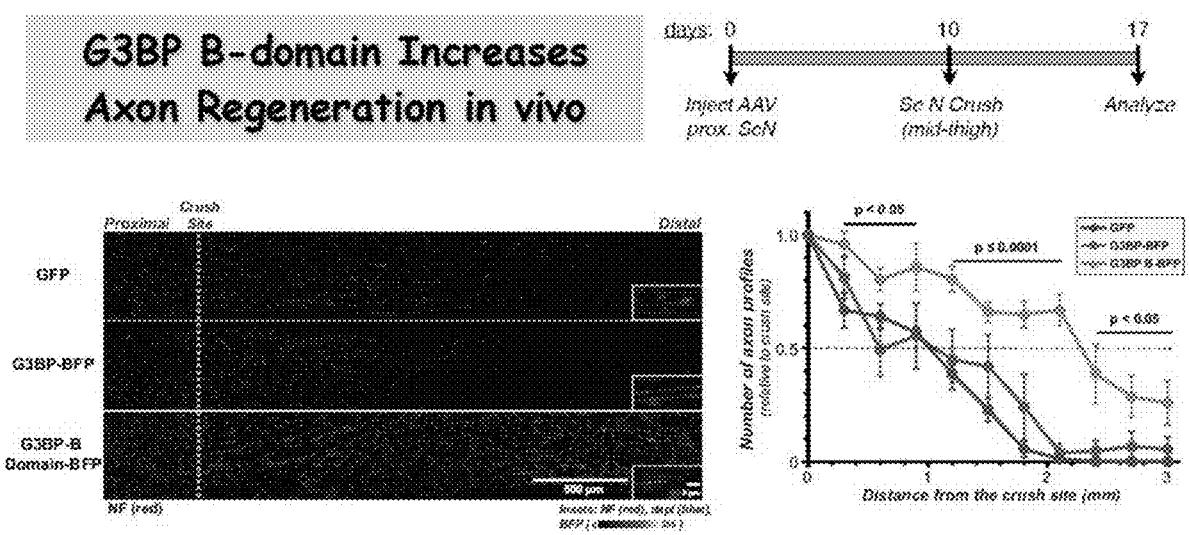
FIG. 6 shows an immunofluorescence comparison and a graph illustrating that G3BP B-domain increases axon regeneration in vivo.

FIG. 6 illustrates that the G3BP1 B domain increases axon regeneration in vivo. Sciatic nerves of adult rats were transduced with adeno-associated virus 5 (AAV5) encoding GFP, G3BP1-BFP (full length G3BP1) or G3BP1-B domain-BFP. After seven (7) days for expression of the virus, the animals underwent sciatic nerve crush at mid-thigh. Seven (7) days later the animals were euthanized and analyzed for axon regeneration. Representative images of immunofluorescence for axonal marker neurofilament are shown on the left for each condition. The graph on the right shows the extent of regeneration. As FIG. 6 illustrates, regeneration is significantly enhanced by introducing the G3BP B domain.

Figure 7:
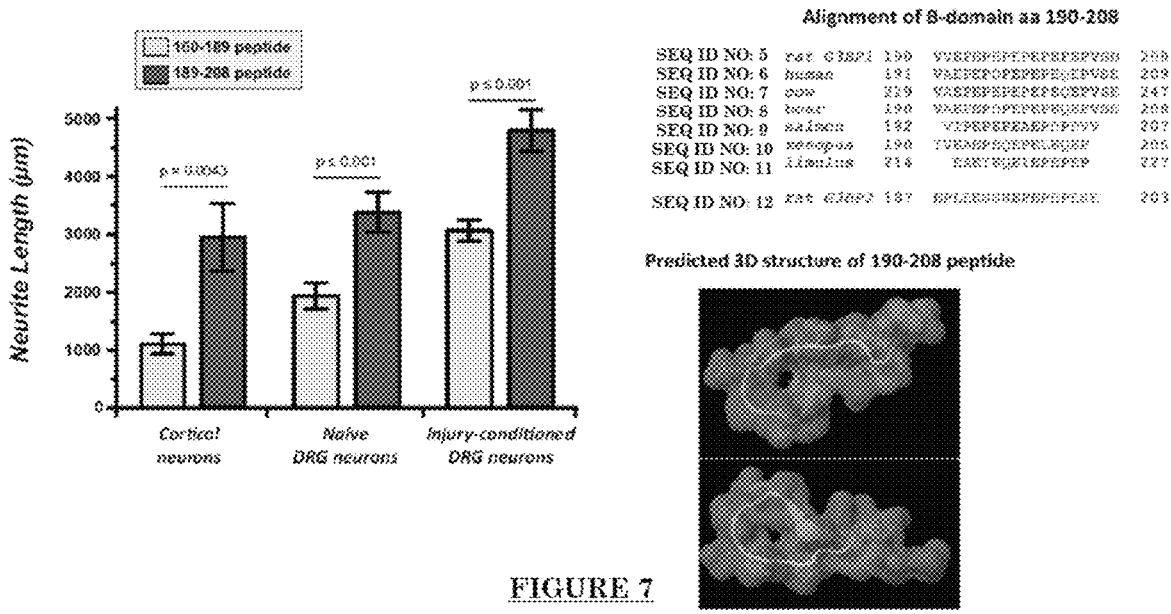
FIG. 7 shows a graph illustrating that the peptide for G3BP1 residues supports axon growth in both PNS and CNS neurons as well as a predicted 3D structure of the peptide.

FIG. 7 shows that the peptide for G3BP1 residues 190-208 supports axon growth in both peripheral nervous system and central nervous system neurons. As FIG. 7 shows, axon growth analyses for embryonic cortical neurons and naive or injury-conditioned adult dorsal root ganglion (DRG) neurons treated with cell permeable peptides corresponding to G3BP1 residues 160-189 or 190-208 are shown. The peptides were designed in house and synthesized by Bachem. The DRG neurons were treated with peptides by whole bath application after twelve (12) hours in culture and analyzed twenty-four (24) hours later. These data show that the 190-208 peptide can effectively increase axon growth in both naive and injury-conditioned neurons. Cortical neurons were cultured in a microfluidic device for three (3) days and then G3BP1 peptides were bath applied to only the axonal compartment. As FIG. 7 illustrates, the 190-208 peptide significantly increased axon growth in CNS neurons. Protein sequence alignments for corresponding regions of 190-208 peptide are shown in the upper right. The lower right shows predicted tertiary structure of rat 190-208 peptide with approximately 180 degree vertical rotation between views. The acidic side chains of glutamates can be seen arrayed along the periphery of the structure.

Critical functions of intra-axonally synthesized proteins are thought to depend on regulated recruitment of mRNA from storage depots in axons. The current disclosure shows that axotomy induces translation of stored axonal mRNAs via regulation of the stress granule protein G3BP1, to support regeneration of peripheral nerves. G3BP1 aggregates in axons of peripheral nerves in stress granule-like structures that decrease during regeneration, with a commensurate increase in phosphorylated G3BP1. Colocalization of G3BP1 with axonal mRNAs is also correlated with the growth state of the neuron. Disrupting G3BP functions by overexpressing a dominant-negative protein disassembles axonal stress granule-like structures, activates intra-axonal mRNA translation, increases axon growth in cultured neurons and accelerates nerve regeneration in vivo.

Injured axons in the peripheral nervous system (PNS) use locally translated proteins for retrograde injury-signaling and regenerative growth. Translation of axonal mRNAs can be activated by different stimuli including axotomy in mature neurons and in response to guidance cues in developing neurons, indicating that a significant fraction of axonal mRNAs are stored until a particular stimulus activates their translation. Stress granules (SG) serve as storage depots for mRNAs in non-neuronal systems, providing a mechanism to respond to cellular stress by sequestering unneeded mRNAs from translation. Aggregation-prone mutations of the SG protein TIA1 and the RNA binding protein TDP-43 have been shown to cause SG aggregation in neurons, but it is not known if SGs have roles in normal function of neurons. Further, although SGs have been detected in dendrites, it is not clear if functional SGs are assembled in axons. The RasGAP SH3 domain binding protein 1 (G3BP1) interacts with the 48S pre-initiation complex when translation is stalled, and it assembles SGs by virtue of its NTF2-like domain. The current disclosure shows that translation of specific axonal mRNAs is negatively regulated in intact axons by G3BP1, but in regenerating peripheral nerves post injury, this negative regulation is removed by dispersion of aggregated G3BP1, to then support accelerated axon growth. When phosphorylated on serine 149 (G3BP1$^{PS149}$), G3BP1's oligomerization is blocked and SGs disassemble, presumably releasing bound mRNAs for translation. Loss of G3BP1 aggregation in SG-like structures in regenerating axons is accompanied by an increase in phosphorylated G3BP1. Disrupting G3BP1 function with a dominant-negative approach activates intra-axonal mRNA translation, increases axon growth in cultured neurons and accelerates nerve regeneration in vivo, and therefore represents a new pro-regenerative therapeutic approach.

Results

Axonal G3BP1 Aggregates Decrease During Nerve Regeneration—

Figure 8A:
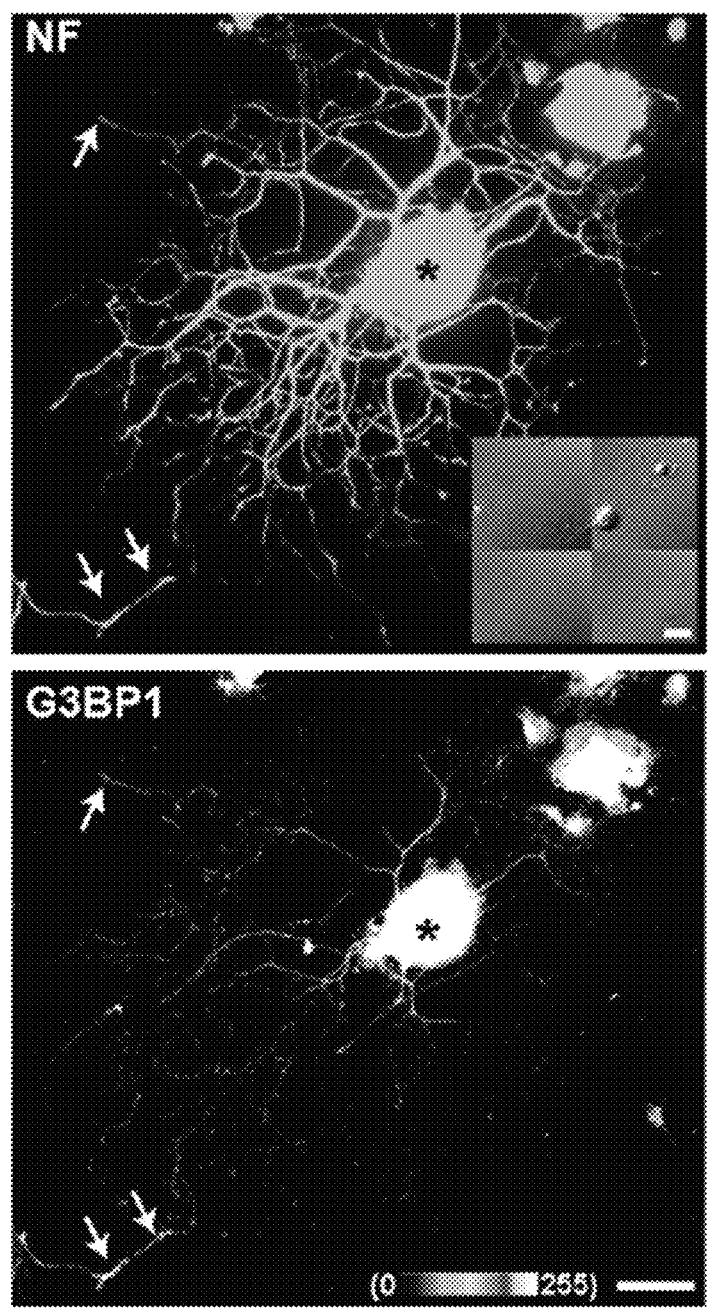
FIG. 8A shows Immunofluorescence for G3BP1 shows signals in cell body (asterisk) and along distal neurites (arrows) in a cultured DRG neuron.
Figure 8B:
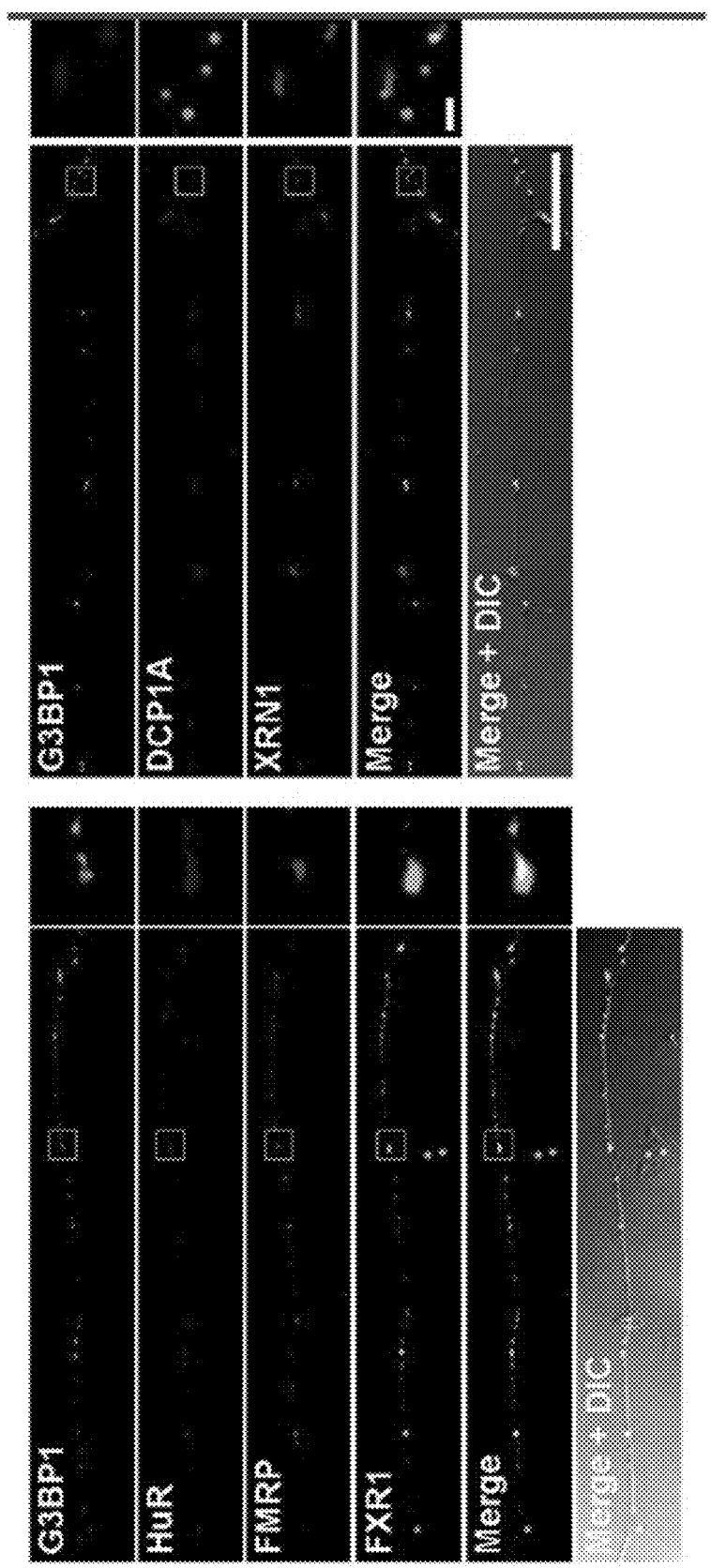
FIG. 8B shows single optical planes for axons of naïve DRG cultures.

The current disclosure investigated if axons of cultured primary sensory neurons contain G3BP1 stress granule-associated protein. Sensory neurons from adult rat dorsal root ganglia (DRG) show strong immunoreactivity for G3BP1 in cell bodies and focally along their axons, see FIG. 8A. FIG. 8A shows Immunofluorescence for G3BP1 shows signals in cell body (asterisk) and along distal neurites (arrows) in a cultured DRG neuron. Previous work has shown that neurites of these adult DRG neurons have axonal features and lack dendritic features; we will use 'axon' for describing these hereafter [scale bar=50 μm]. Axonal G3BP1 signals showed higher colocalization with known SG components than components of processing bodies (PB) that are linked to RNA degradation (FIGS. 8B and 8C). These axonal G3BP1 aggregates are smaller than those described for SGs in non-neuronal cells (diameter ~0.2-0.8 μm vs. ≥1 μm), so the axonal SG-like structures approximate the ~250 nm diameter described for SG core structure. FIGS. 8B and 8C show single optical planes for axons of naïve DRG cultures co-labeled for G3BP1, HuR, FMRP and FXR1 or G3BP1, DCP1A and XRN1 are shown as indicated; boxed region represents the area higher magnification images are taken from (FIG. 8B). Axonal G3BP1 shows higher colocalization coefficients (FIG. 8C) for SG proteins than PB proteins (N≥30 axons over 3 repetitions) [scale bar=10 μm for large panels and 1 μm for small panels]. PLA shows higher colocalization for G3BP1 and HuR than G3BP1 and DCP1A in axons. Confocal microscopy of sciatic nerve sections showed robust G3BP1 signals overlapping neurofilament (NF). Using imaging parameters standardized for detection of aggregated G3BP1, intra-axonal G3BP1 was found to be much lower in the axons proximal to the crush site in 7 d post-injury nerves (FIG. 8E). Axons are actively regenerating at 7 d after nerve crush (see Extended Data S5B at FIG. 17B), thus, the current disclosure considered if the decrease in axonal SG-like structures is a feature of growing axons.

Figure 8D:
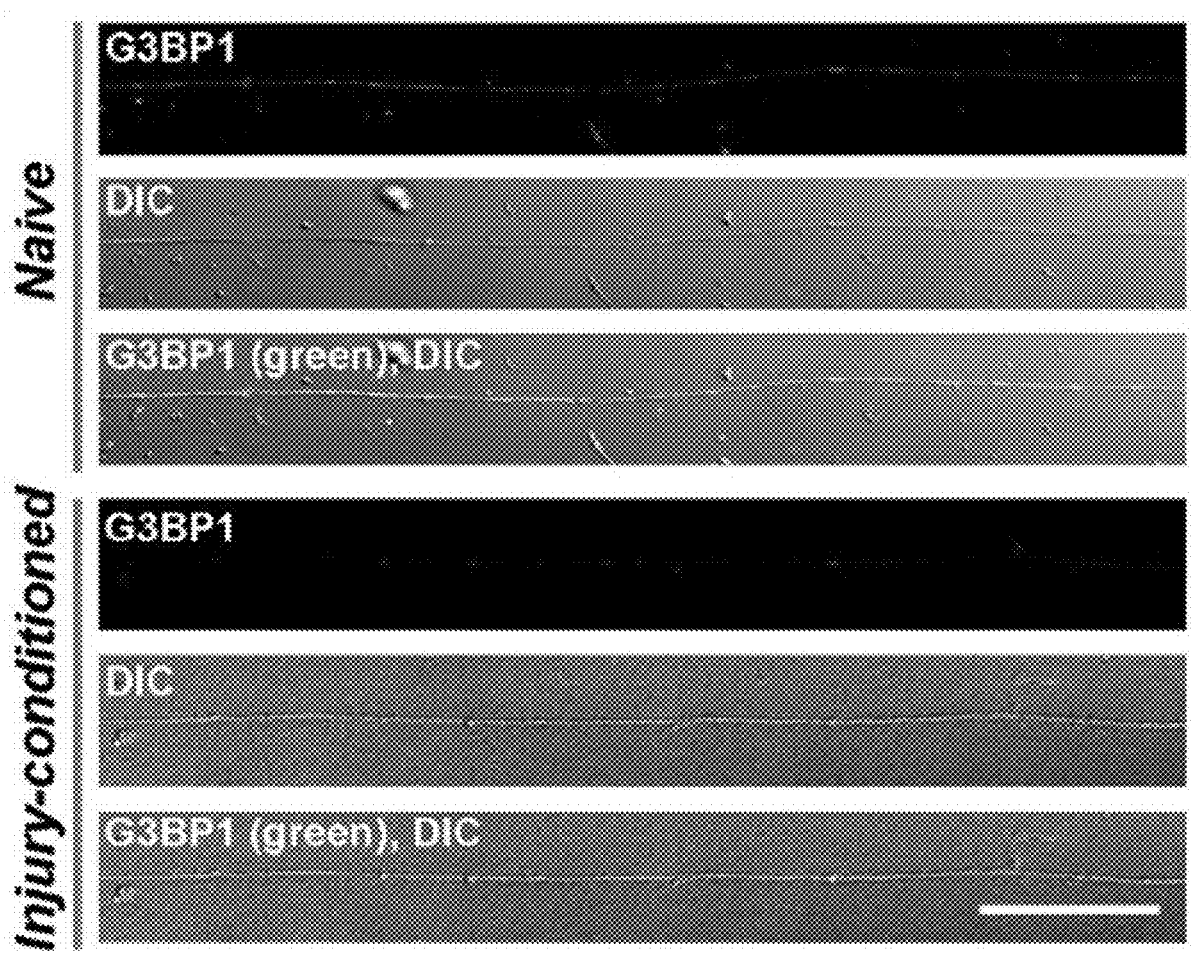
FIG. 8D shows exposure-matched images of G3BP1 in distal axons of DRGs cultured from naïve vs. 7 day injury conditioned animals.
Figure 8E:
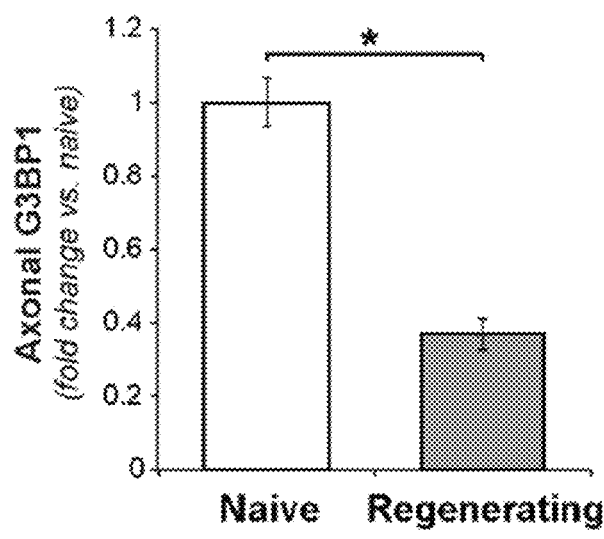
FIG. 8E shows quantification of axonal G3BP1 immunoreactivity from sciatic nerve.
Figure 8F:
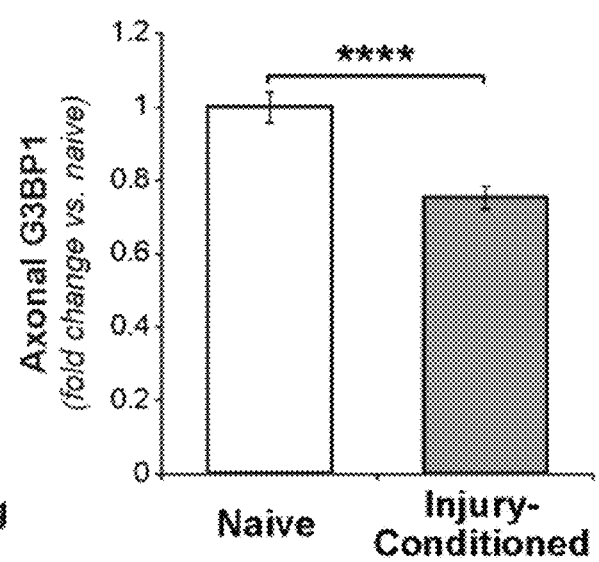
FIG. 8F shows quantification of axonal G3BP1 immunoreactivity from axons of cultured DRG neurons.

DRG neurons that are conditioned by an in vivo crush injury 7 days prior to culture show more rapid axonal outgrowth over 18-48 h in vitro compared to uninjured (naïve) DRGs, and the rapidly growing axons of injury-conditioned neurons showed decreased levels of G3BP1 aggregates compared to those of naïve DRG cultures (FIGS. 8D and 8F).

G3BP1 is Phosphorylated in Regenerating Axons—

Figure 9A:
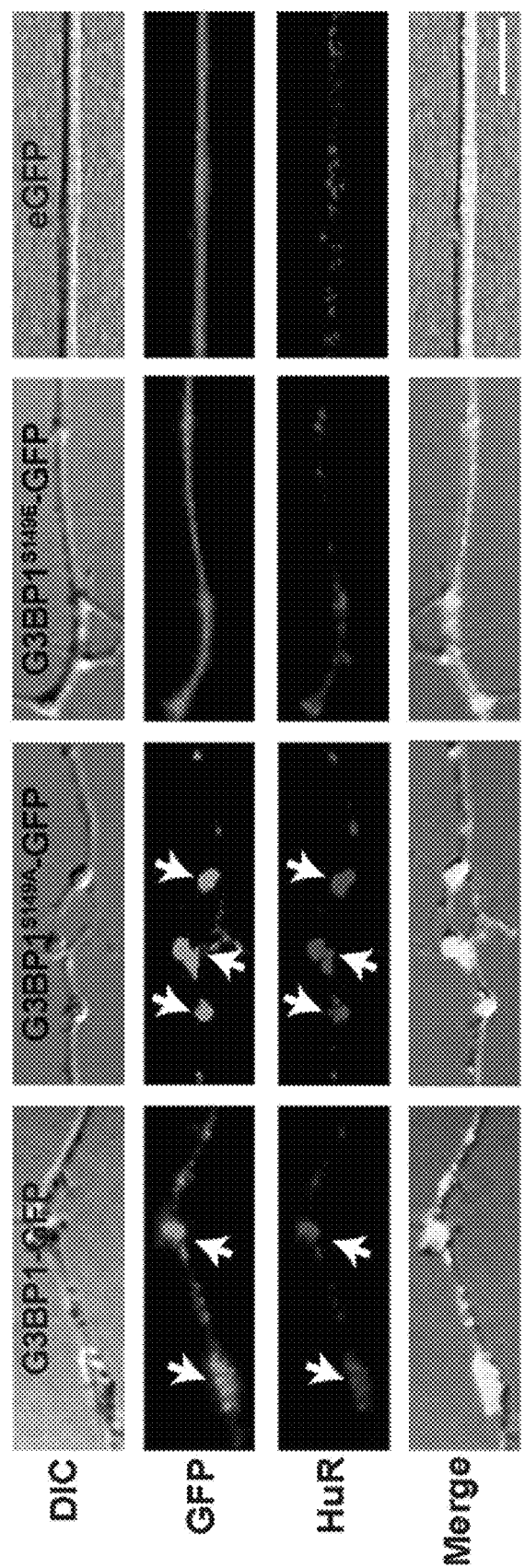
FIG. 9A shows axons of DRG neurons transfected with indicated G3BP1 constructs vs. eGFP.
Figure 9B:
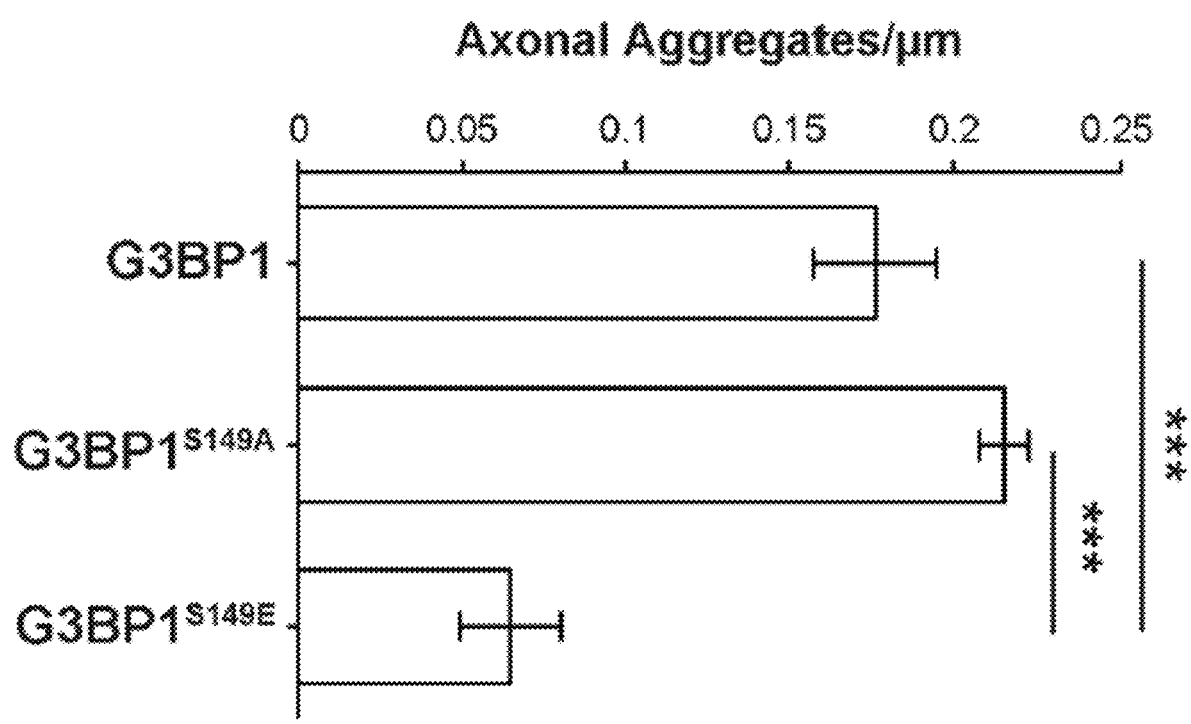
FIG. 9B shows quantification of axonal aggregates for G3BP1-GFP, G3BP1$^{S149A}$-GFP, and G3BP1$^{S149E}$-GFP.
Figure 9C:
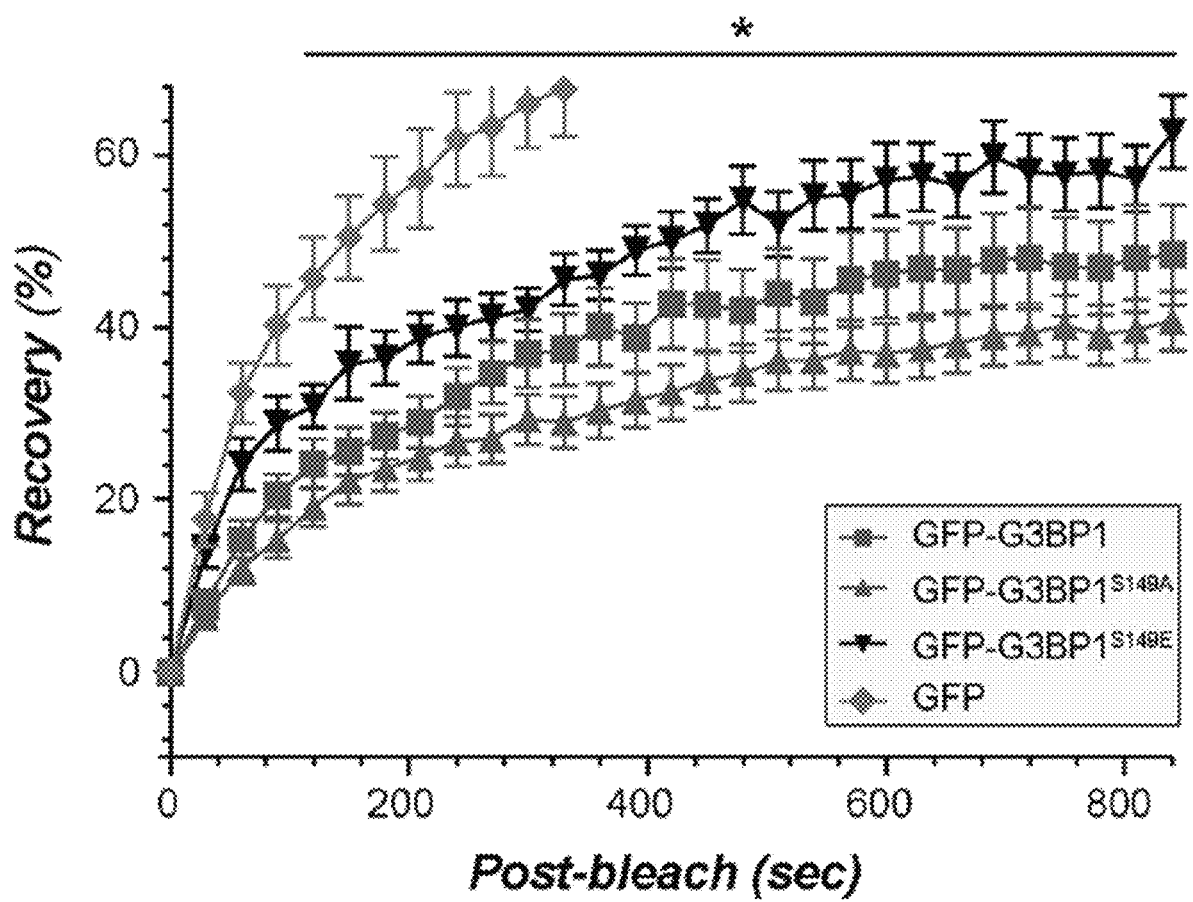
FIG. 9C shows Flourescence Recovery After Photobleaching (FRAP) analyses for neurons transfected with constructs from FIG. 9B.
Figure 9D:
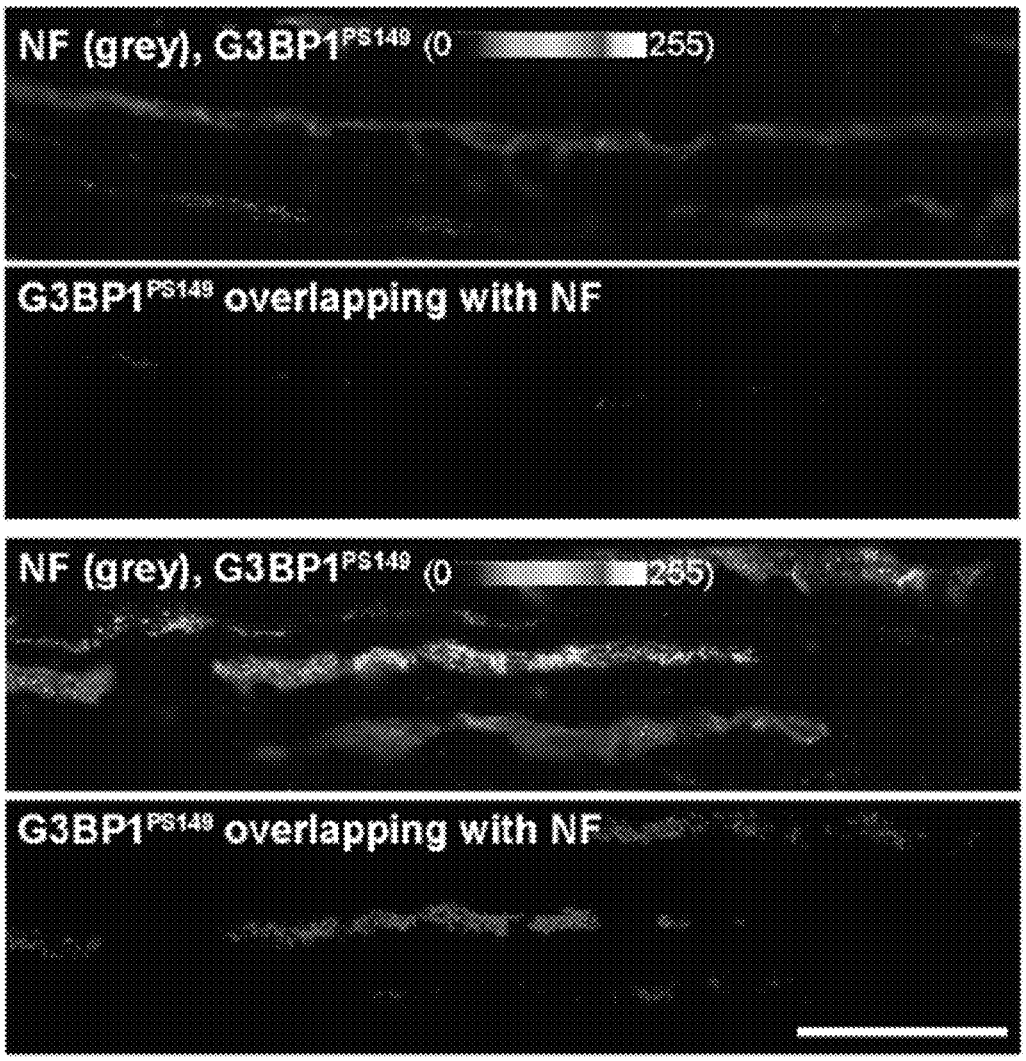
FIG. 9D shows exposure-matched confocal images for G3BP1$^{PS149}$ and neurofilament (NF) for sciatic nerve as in FIG. 8D.
Figure 9E:
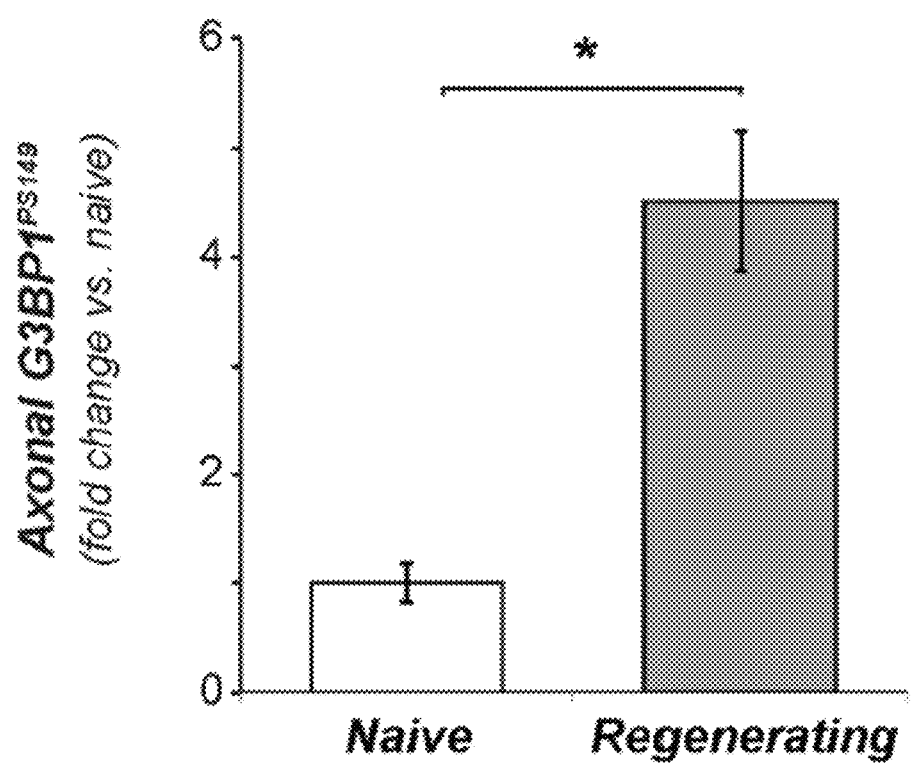
FIG. 9E shows quantification of the signals of FIG. 9D.
Figure 13A:
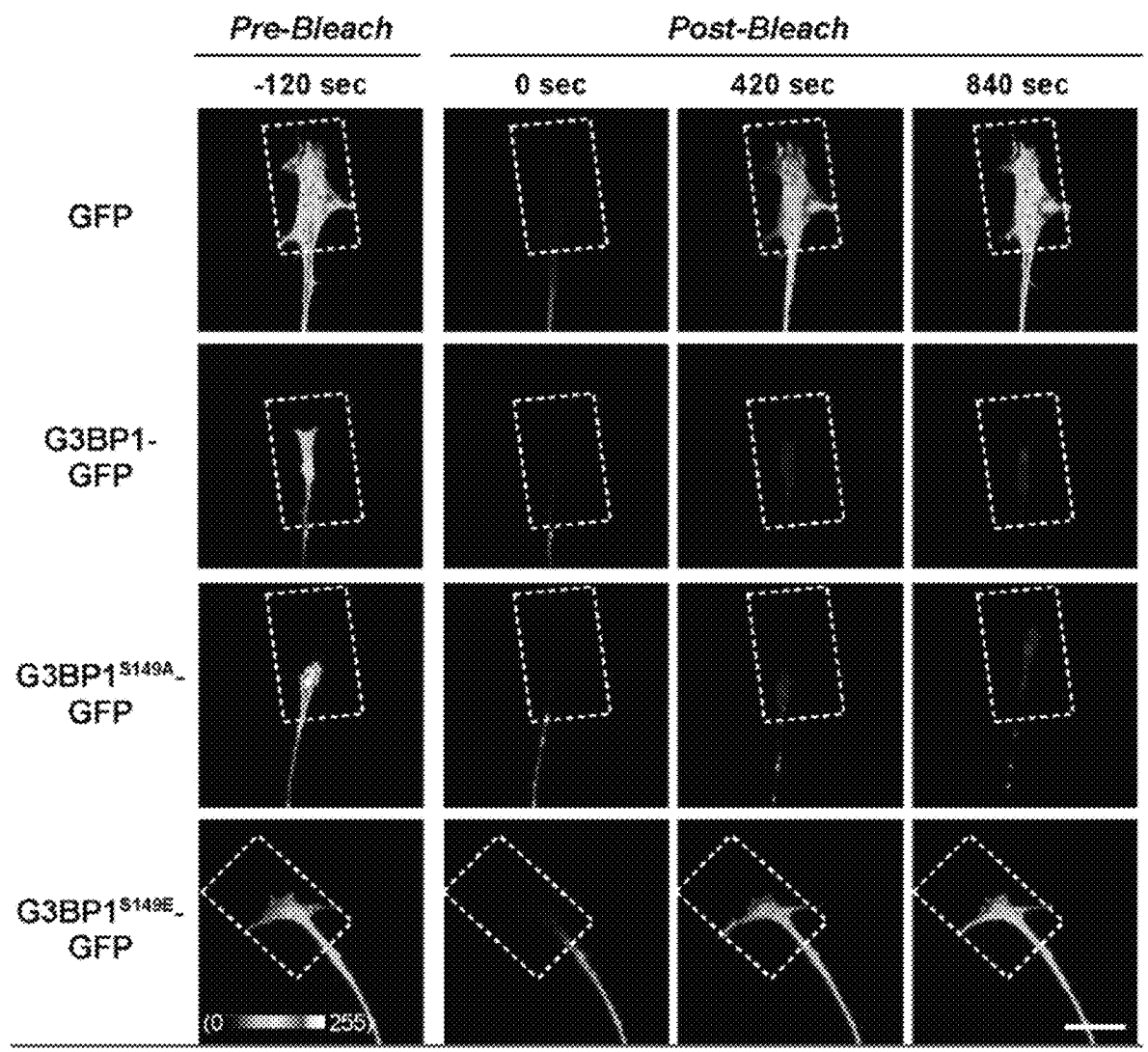
FIG. 13A shows representative FRAP image sequences.

To determine if phosphorylation alters aggregation of axonal G3BP1, the current disclosure expressed non-phosphorylatable and phosphomimetic G3BP1 mutants (G3BP1$^{S149A}$-GFP and G3BP1$^{S149E}$-GFP, respectively) in cultured DRGs. Axonal G3BP1$^{S149A}$-GFP showed aggregated signals that overlapped with HuR, while axonal G3BP1$^{S149E}$-GFP appeared diffuse (FIGS. 9A and 9B). G3BP1$^{S149E}$GFP also showed significantly higher mobility in axons than G3BP1$^{S149A}$-GFP, GFP, and G3BP1-GFP showed mobility intermediate between G3BP1$^{S149E}$-GFP and G3BP1$^{S149A}$-GFP (FIG. 9C, FIG. 13A). This is consistent with G3BP1$^{S149A}$-GFP aggregating into SG-like structures in axons. Axonal G3BP1$^{PS149}$ immunoreactivity was increased in regenerating compared to uninjured nerves (FIGS. 9D and 9E).

Thus, axonal injury decreases the prevalence of axonal SG-like structures, and this correlates with an increase in axonal G3BP1$^{PS149}$ levels. Moreover, the ratio of axonal G3BP1$^{PS149}$ to axonal G3BP1 aggregates increases in distal axons and growth cones (FIGS. 9F and 9G), indicating that the axonal SG-like structures are dynamically regulated along the growing axon.

Axonal G3BP1 Modulates Axonal mRNA Translation—

Figure 10A:
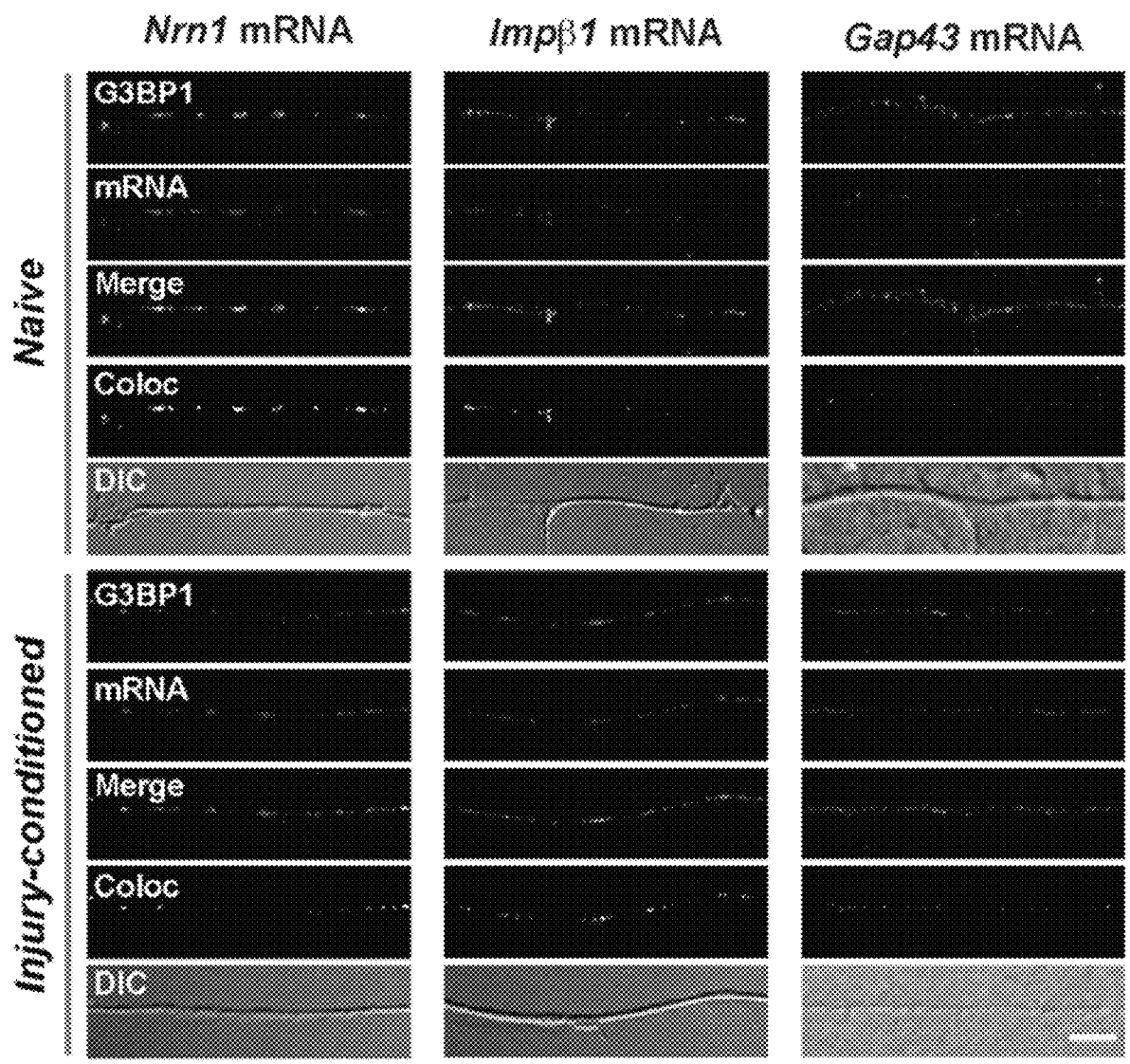
FIG. 10A shows images of Fluorescence in situ Hybridization (FISH) plus IF for indicated mRNAs and G3BP1 protein for axons of naïve and 7 d injury-conditioned DRG neurons.
Figure 10B:
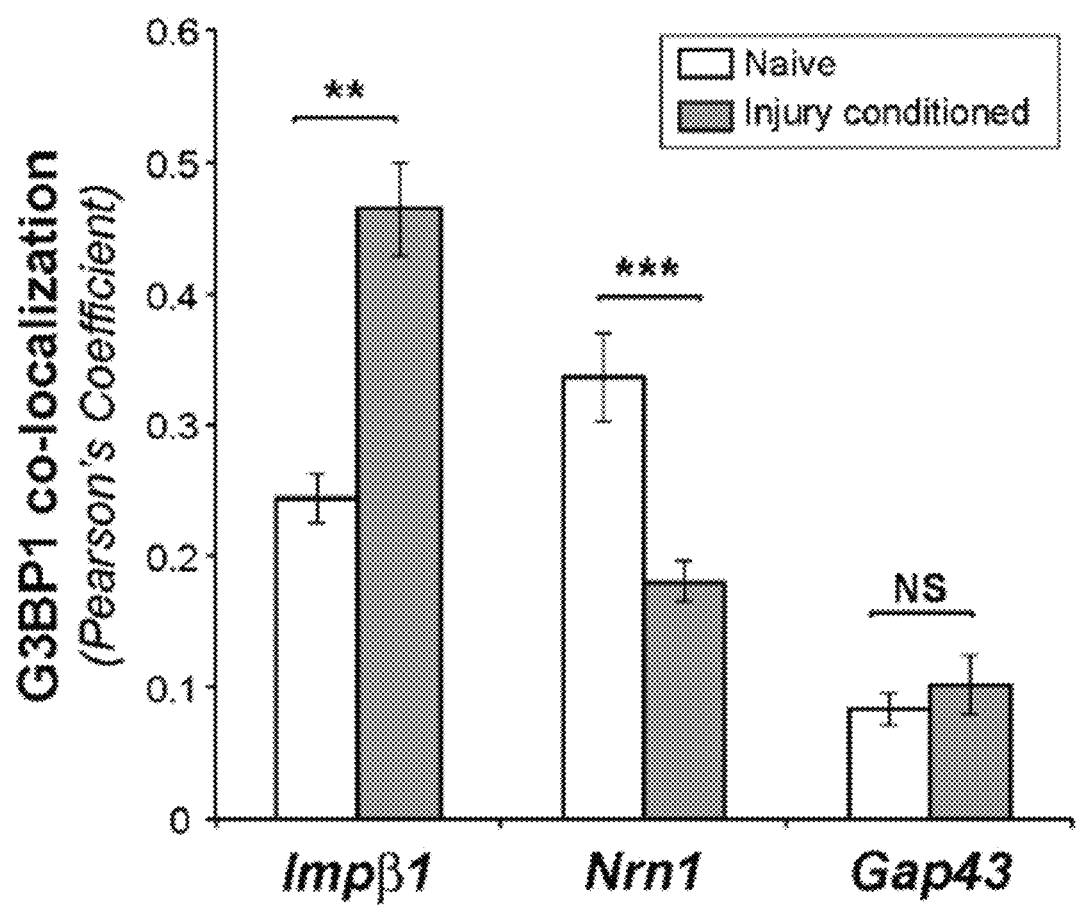
FIG. 10B shows quantification of colocalizations for Nrn1, Impβ1, and Gap43 mRNAs with G3BP1 in axons of neurons cultured from naïve or 7 day injury-conditioned animals.

Previous work has detected ribosomes and translation factors in regenerating PNS axons in vivo, so the decrease in SG-like structures in distal axons could reflect increased axonal protein synthesis. Thus, the current disclosure considered if axonal mRNAs colocalize with G3BP1 in cultured neurons. Endogenous Neuritin1 (Nrn1) and Importin β1 (Impβ1) mRNAs showed clear colocalization with axonal G3BP1, but Gap43 mRNA did not (FIG. 10A). The more rapidly growing axons of injury-conditioned DRG neurons showed higher colocalization of Impβ1 with G3BP1 than those of naïve DRGs, while axonal Nrn1 showed the opposite (FIG. 10B). Axonal Gap43 also showed overall lower G3BP1 colocalization coefficients that did not change with injury conditioning (FIG. 10B). These distinct colocalizations of axonal Impβ1 and Nrn1 with G3BP1 in naïve vs. injury-conditioned neurons likely reflect different functions of the encoded proteins in these different growth states.

Figure 10C:
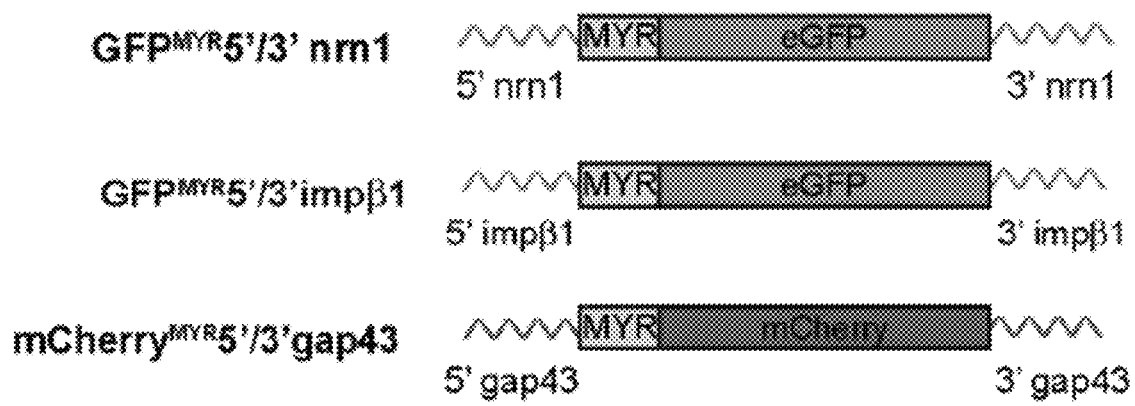
FIG. 10C shows schematics of translation reporter constructs used in panels d-f.

The current disclosure moved to fluorescent reporters to determine if axonal SG-like structures contribute to translation. For this, the current disclosure generated axonally targeted GFP$^{MYR}$ and mCherry$^{MYR}$ reporters containing the 5' and 3' untranslated regions (UTR) of Impβ1, Nrn1, and Gap43 mRNAs (GFP$^{MYR}$5'/3'impβ1, GFP$^{MYR}$5'/3'nrn1, and mCh$^{MYR}$5'/3'gap43, respectively; FIG. 10C). The membrane localizing myristoylation (MYR) of the fluorescent reporter proteins dramatically limits their diffusion from sites of translation, so these have provided a surrogate for localized protein synthesis in dendrites and axons using fluorescence recovery after photobleaching (FRAP). The 3' (Impβ1 and Gap43) and 5' (Nrn1) UTRs provide axonal targeting for reporter mRNAs, and with both 5' and 3'UTRs, the reporter approximates the translational regulation of the endogenous mRNAs.

Figure 14A:
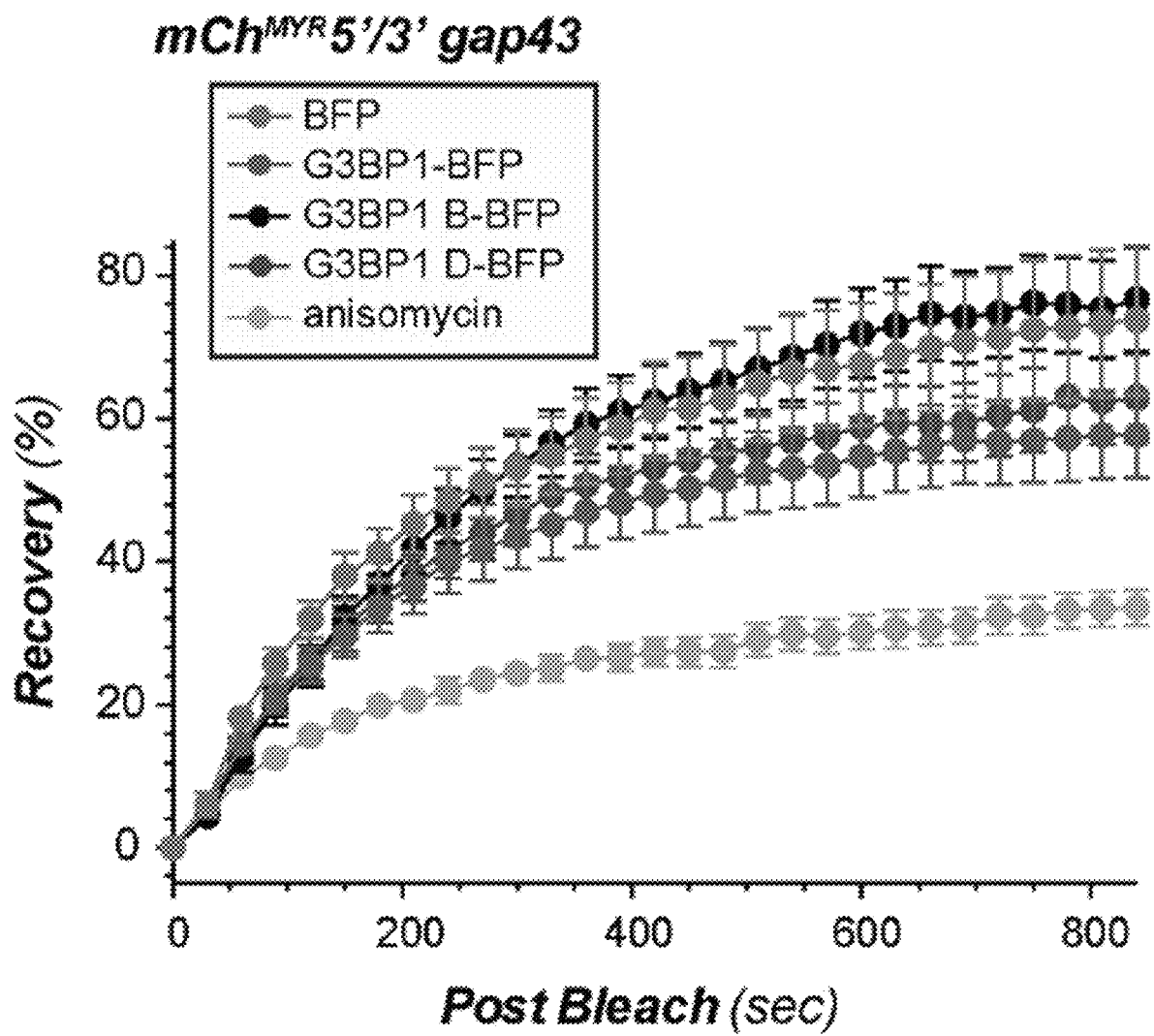
FIG. 14A shows FRAP analyses for DRGs expressing mCh$^{MYR}$5'/3'gap43 plus the indicated G3BP1-BFP constructs or BFP control.

Recovery of axonal GFP$^{MYR}$5'/3'impβ1 and GFP$^{MYR}$5'/3'nrn1 fluorescence was decreased in DRGs expressing G3BP1-BFP compared to the BFP control (FIGS. 10D, 10E and 10F), but mCh$^{MYR}$5'/3'gap43 recovery was not significantly affected by G3BP1-BFP expression (FIG. 14A). Treatment with translation inhibitors confirmed that the fluorescence recovery in axons after photobleaching represents new protein synthesis (FIGS. 10E, 10F, and FIG. 14A). Treatment with translation inhibitors confirmed that the fluorescence recovery in axons after photobleaching represents new protein synthesis (FIGS. 10E and 10F, Extended Data FIG. 2a at FIG. 14A). Furthermore, RNA immunoprecipitation (RIP) analyses showed enrichment of GFP$^{MYR}$5'/3'impβ1 and GFP$^{MYR}$5'/3'nrn1, but not mCh$^{MYR}$5'/3'gap43, in G3BP1 immunoprecipitates (FIG. 10G).

Acidic domain of G3BP1 increases axonal growth—

Figure 11A:
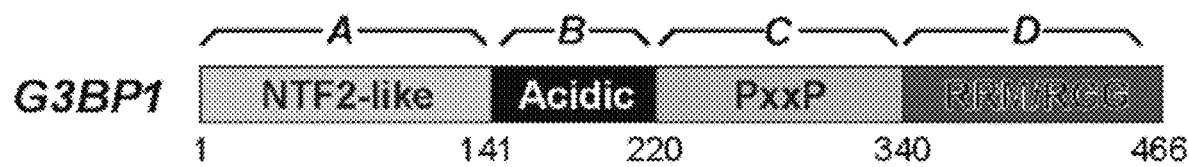
FIG. 11A shows a schematic of G3BP1 domains as defined by Tourriere et al. (2003).
Figure 11B:
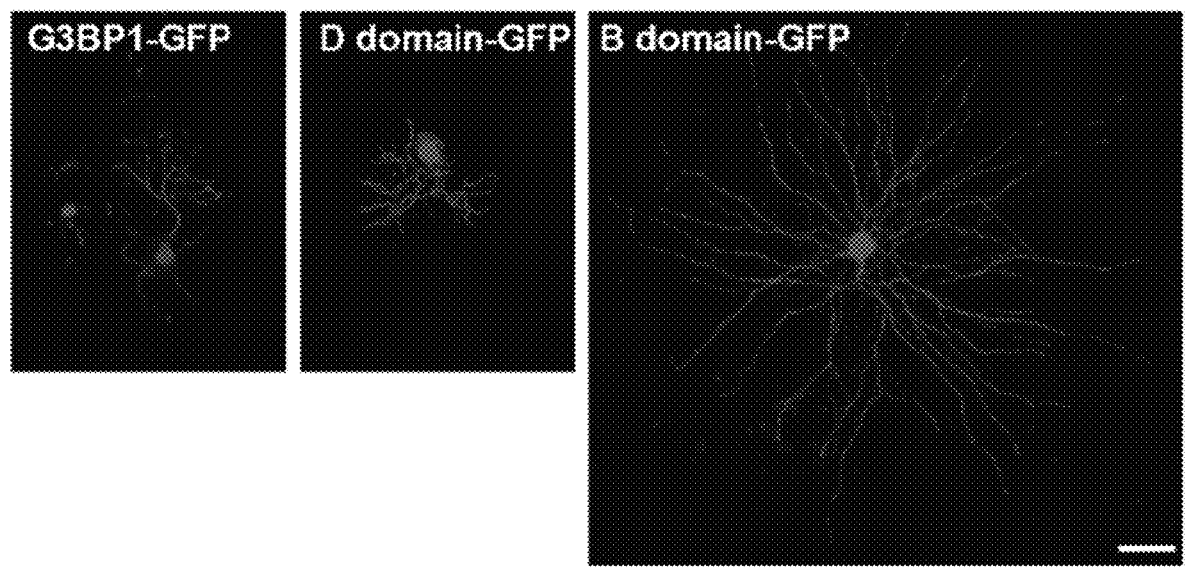
FIG. 11B shows representative images for NF-labeled DRG neurons transfected with indicated constructs.
Figure 15B:
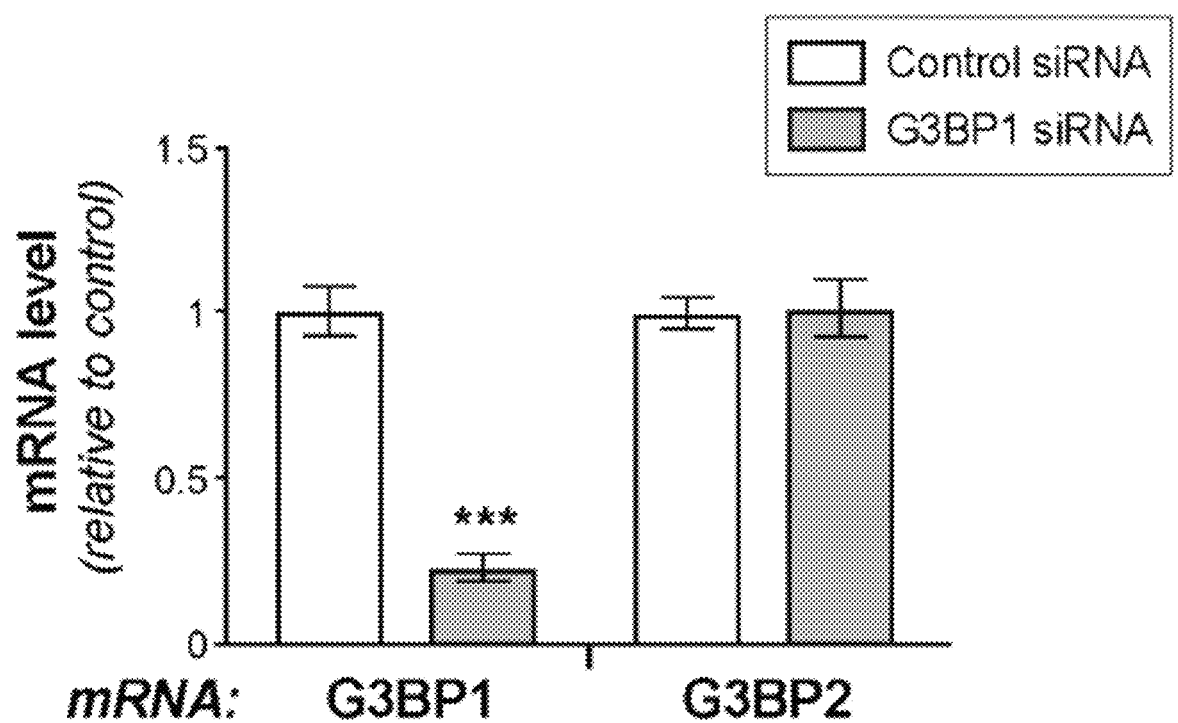
FIG. 15B shows RT-ddPCR analyses of G3BP1 and G3BP2 mRNA levels in DRGs transfected with control (siCntl) and G3BP1 (siG3BP1) siRNAs.
Figure 15C:
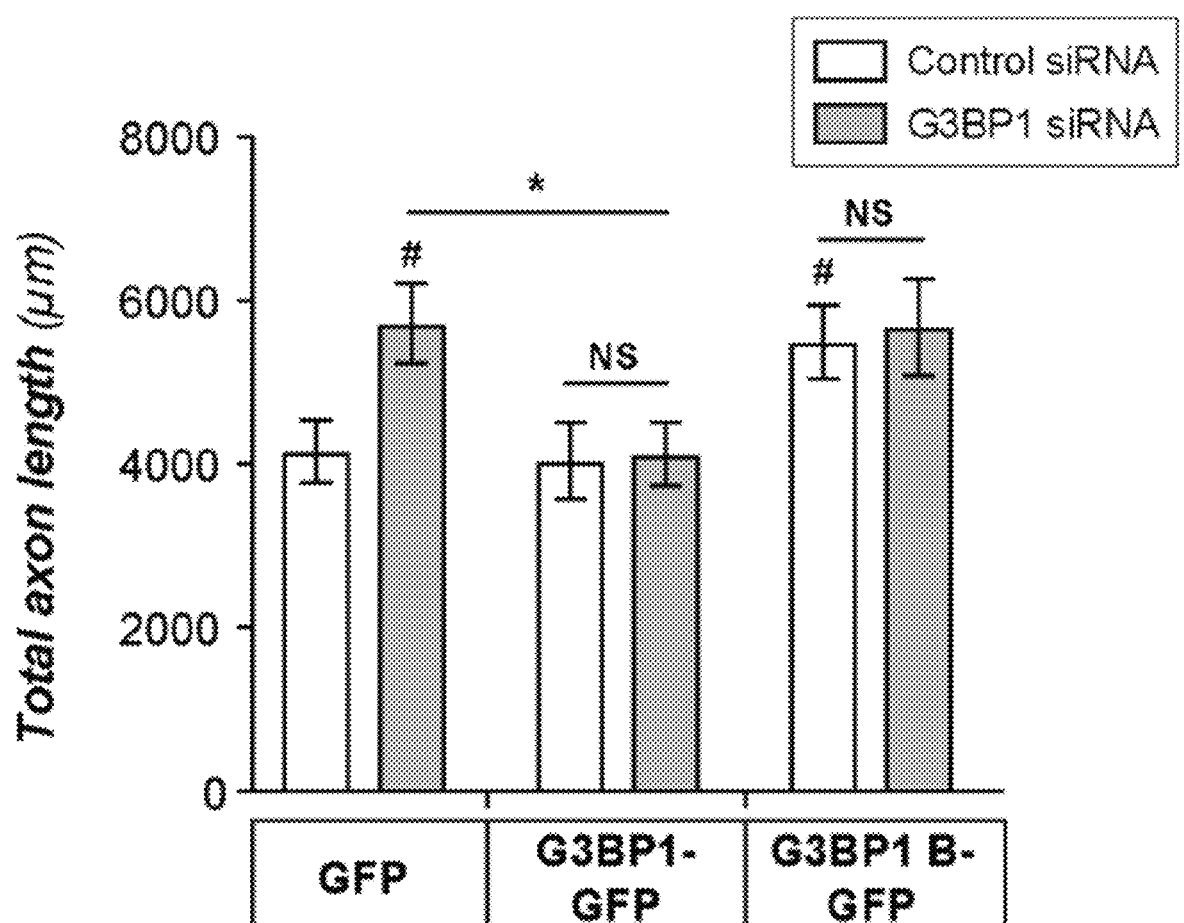
FIG. 15C shows axon growth data for DRG neurons transfected with control (siCntl) or G3BP1 (siG3BP1) siRNAs plus GFP, G3BP1-GFP, or G3BP1 B domain-GFP.
Figure 17A:
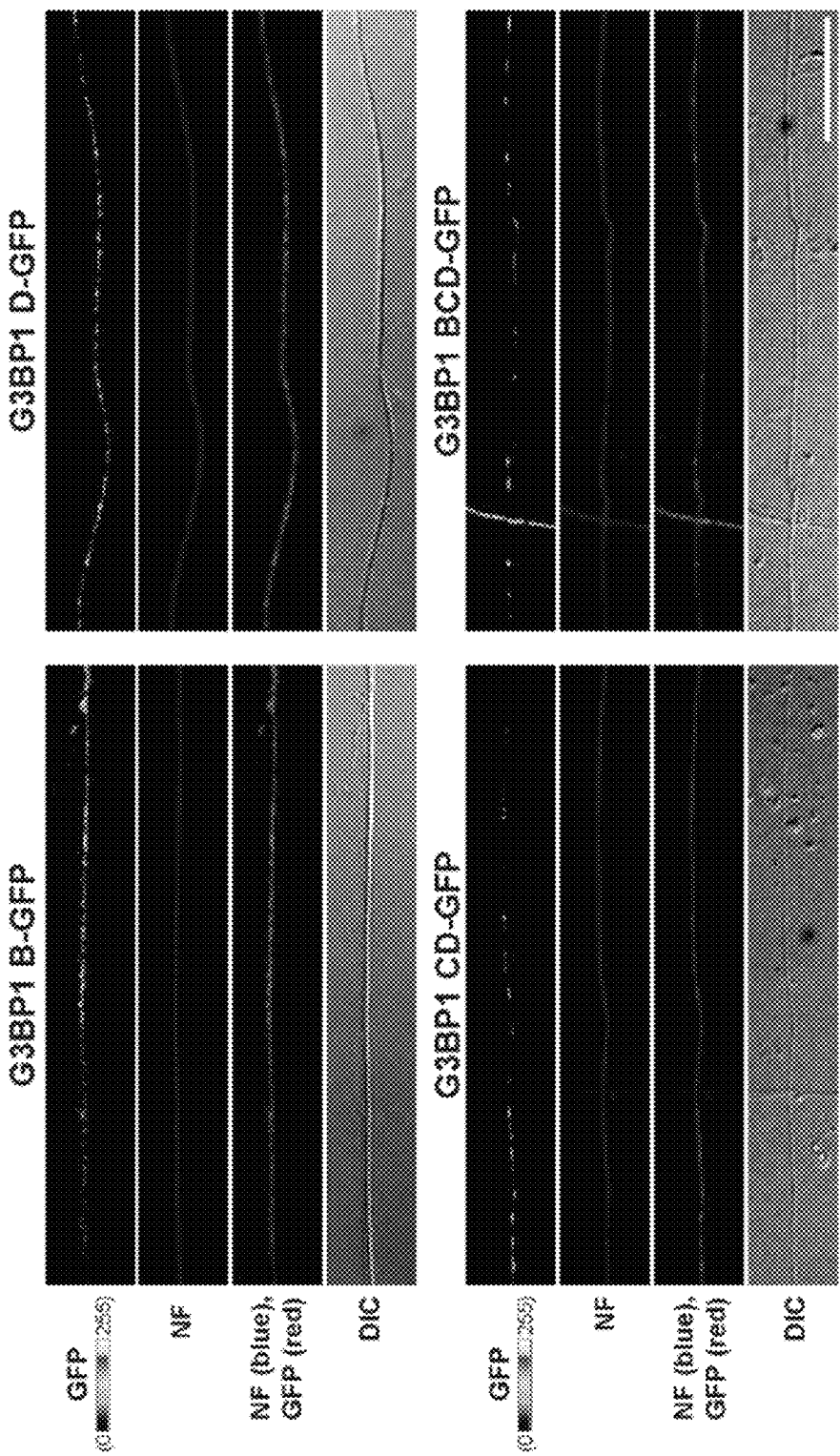
FIG. 17A shows representative images of distal axons of naïve DRG neurons were transfected with G3BP1 B domain-GFP, D domain-GFP, CD domain-GFP, or BCD domain-GFP.

G3BP1 is composed of four separate domains: N-terminal NTF2-like 'A domain', a highly acidic 'B domain', PxxP motif containing 'C domain', and Cterminal RNA hinging motif containing 'D domain' (FIG. 11A). Expression of G3BP1 deletion constructs in naive DRG cultures showed that G3BP1 B, CD, BCD and D domain proteins all localized to axons (FIG. 17A). Neurons expressing the G3BP1 B domain showed significantly longer axons, while those expressing the D or CD domains showed shorter axons (FIG. 11B, FIG. 15A). G3BP1 D domain expression decreases protein synthesis in non-neuronal cells through eIF2α phosphorylation. Interestingly, expressing G3BP1 BCD domains together reversed the growth deficit seen for CD, pointing to a dominant effect of the B domain in absence of G3BP1's aggregating NTF2 like region (FIG. 15A). Surprisingly, full-length G3BP1 overexpression had no significant effect on axon growth (FIG. 15A), perhaps indicating that G3BP1 is at saturating levels in DRG neurons. Consistent with this, siRNA-mediated knockdown (KD) of G3BP1 significantly increased axon growth and this was completely reversed by co-transfection with a siRNA-resistant G3BP1-GFP (FIG. 15C). However, co-transfecting with the G3BP1 B domain did not further increase axon length, suggesting that B domain inhibits G3BP1 function. DRG cultures expressing full-length G3BP1-, B domain-, and CD domain-GFP showed modest decline in neurite branching (FIG. 15A).

Figure 11C:
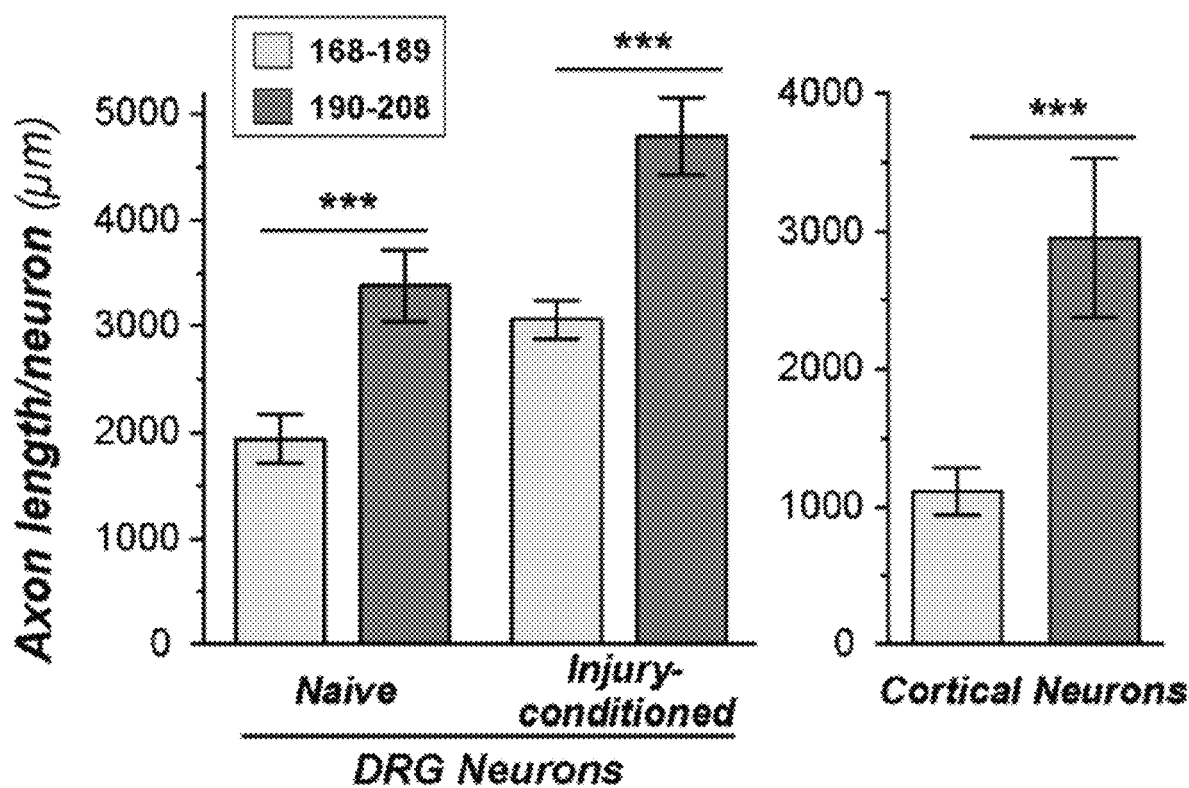
FIG. 11C shows quantitation of axon growth from DRGs (left) and cortical neurons (right) treated with cell-permeable 168-189 or 190-208 G3BP1 peptides is shown.
Figure 16A:
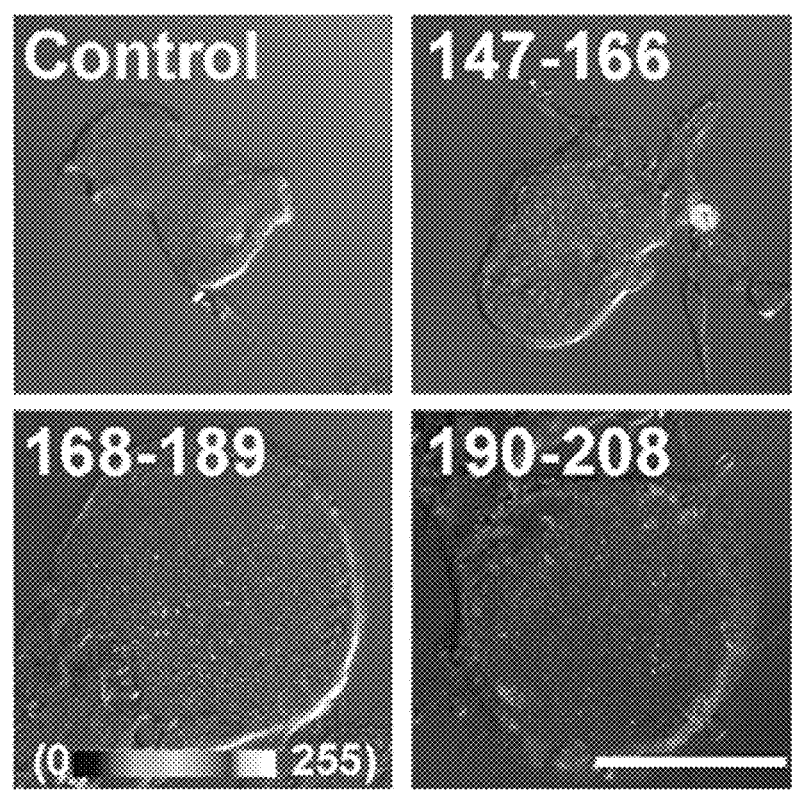
FIG. 16A shows Representative images of dansyl chloride fluorescence of internalized peptides in DRG cell bodies.
Figure 16B:
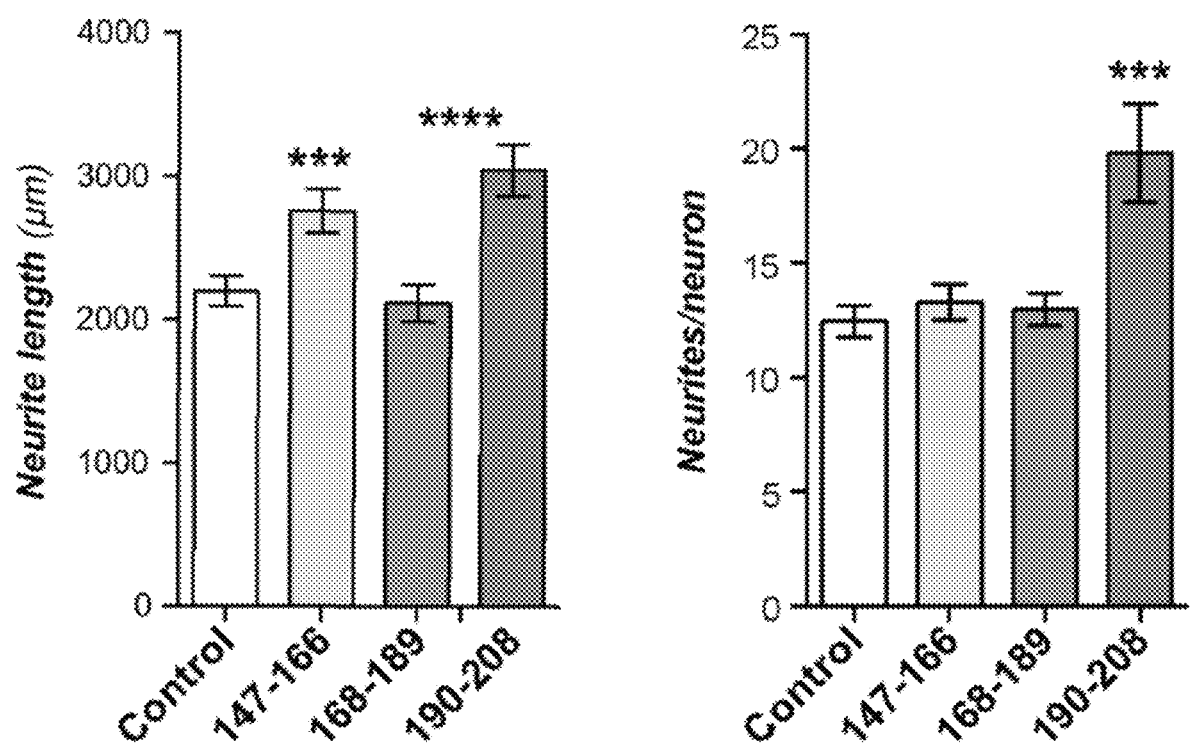
FIG. 16B shows neurite outgrowth analyses for dissociated DRG neurons treated with peptides immediately after plating.
Figure 16C:
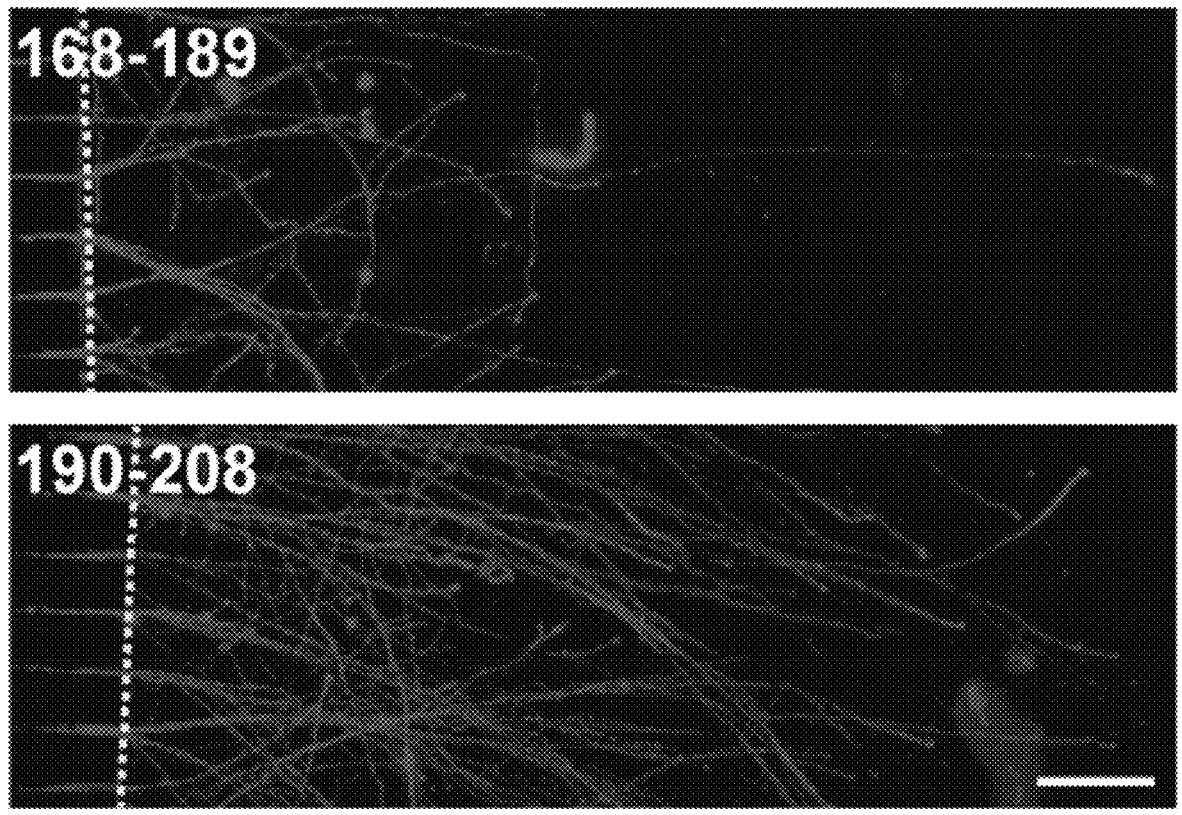
FIG. 16C shows representative images of axonal compartment of microfluidic culture device with cortical neurons stained for tau at DIV 6.

To determine if a smaller region of the G3BP1 B domain is sufficient to increase axon growth, the current disclosure generated fluorescently-labeled, cell-permeable Tat fusion peptides corresponding to residues 147-166, 168-189, and 190-208 of rat G3BP1. Peptides penetrated the neurons in DRG cultures by 30 min. after application (FIG. 16A). When added to DRG cultures immediately after plating, both the 147-166 and 190-208 peptides increased axon length and the 190-208 peptide increased number of neurites per neuron (FIG. 16B). Effects of the 190-208 peptide were significantly stronger, so the current disclosure concentrated efforts on this peptide comparing to the 168-189 peptide. To discriminate between increased axon extension vs. earlier initiation of axon growth, the current disclosure exposed DRG cultures to peptides after the neurons had fully initiated axonal growth. With delayed application, the 190-208 peptide significantly increased axon length in both naive and pre-injured DRG neurons (FIG. 11C). Cortical neuron cultures also showed a significant increase in axon growth when the 190-208 peptide was applied directly to axons (FIG. 11C, FIG. 16C).

G3BP1's Acidic Domain Accelerates PNS Nerve Regeneration—

In light of the increased axon growth seen above, the current disclosure asked if introducing the G3BP1 B domain might alter axon regeneration in vivo. For this, adult rats were transduced with adeno-associated virus (AAV) expressing B or D domains and then subjected to sciatic nerve crush 10 d later.

Figure 11D:
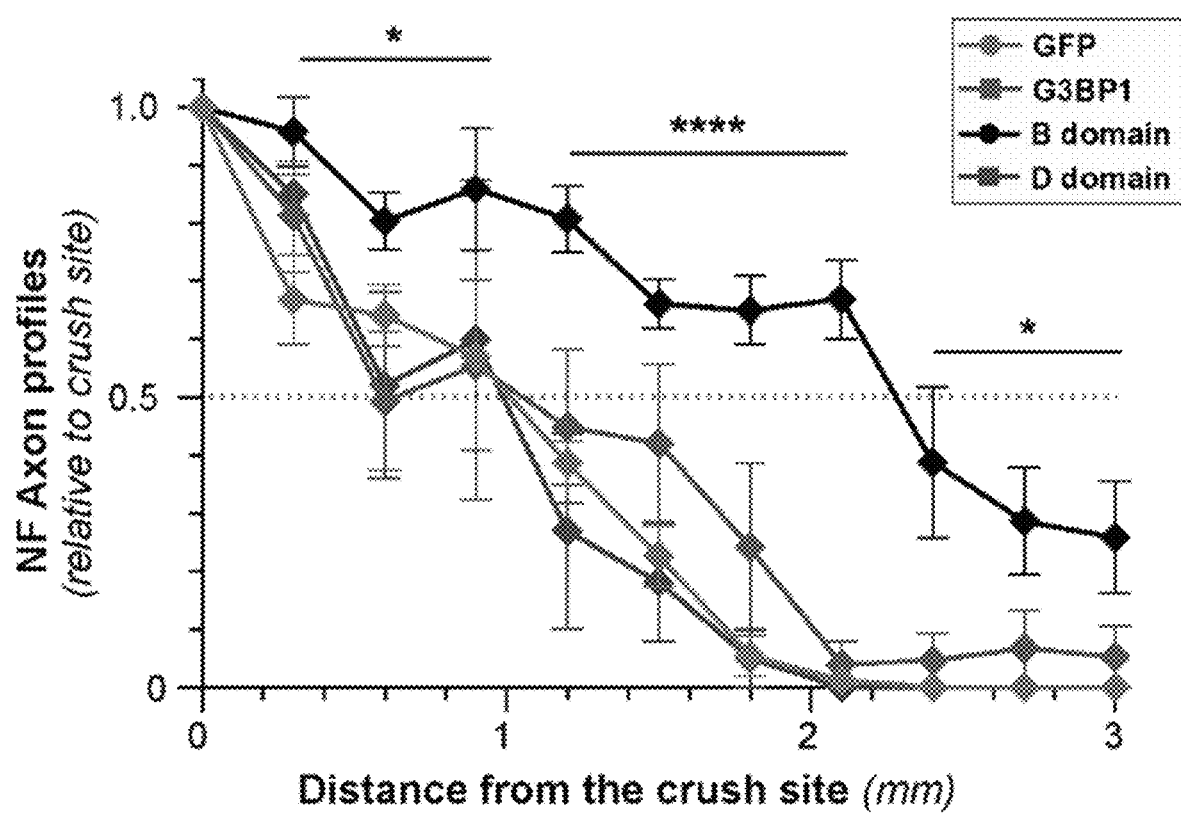
FIG. 11D shows extent of axon regeneration at 7 d post sciatic nerve crush in adult rats transduced with AAV5 encoding G3BP1-BFP, G3BP1 B domain-BFP, G3BP1 D domain-BFP, or GFP control.
Figure 17B:
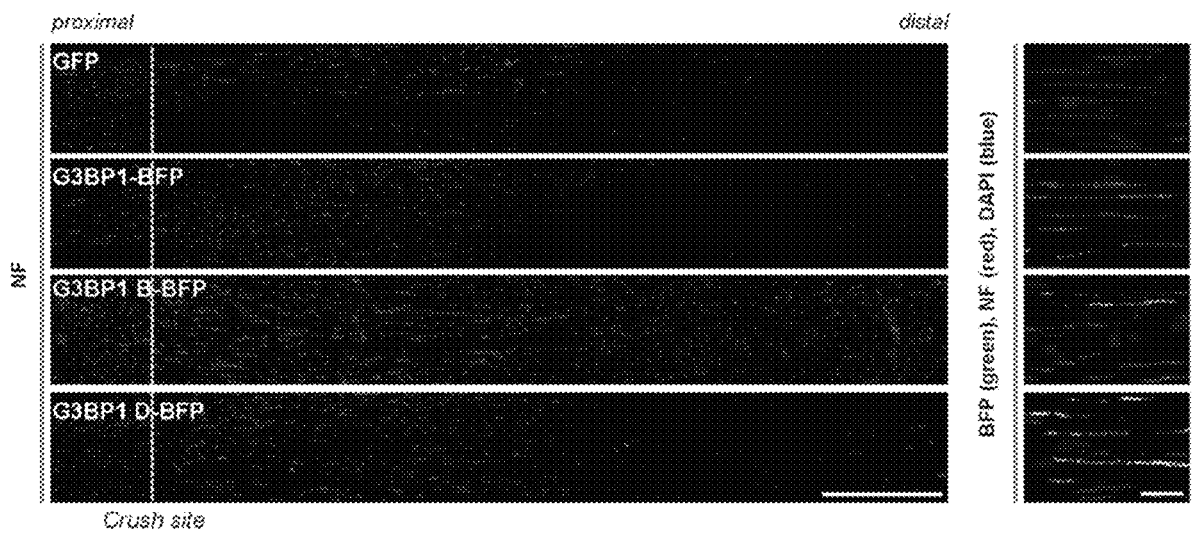
FIG. 17B shows representative, exposure-matched confocal images of crushed sciatic nerves of adult rats transduced with AAV5 encoding the G3BP1-BFP, G3BP1 B domain-BFP, G3BP1 D domain-BFP or GFP.

At 7 d after crush injury (17 d post-transduction), G3BP1-BFP, G3BP1 B domain-BFP, and G3BP1 D domain-BFP were visible in the regenerating sciatic nerve axons (FIG. 17B). The G3BP1 B domain-BFP transduced animals showed significantly increased axon regeneration compared to G3BP1-BFP, and G3BP1 D domain-BFP, and GFP transduced animals (FIG. 11D, FIG. 17B).

G3BP1's acidic domain activates intra-axonal translation through disassembly of stress granule protein aggregates—

Figure 12A:
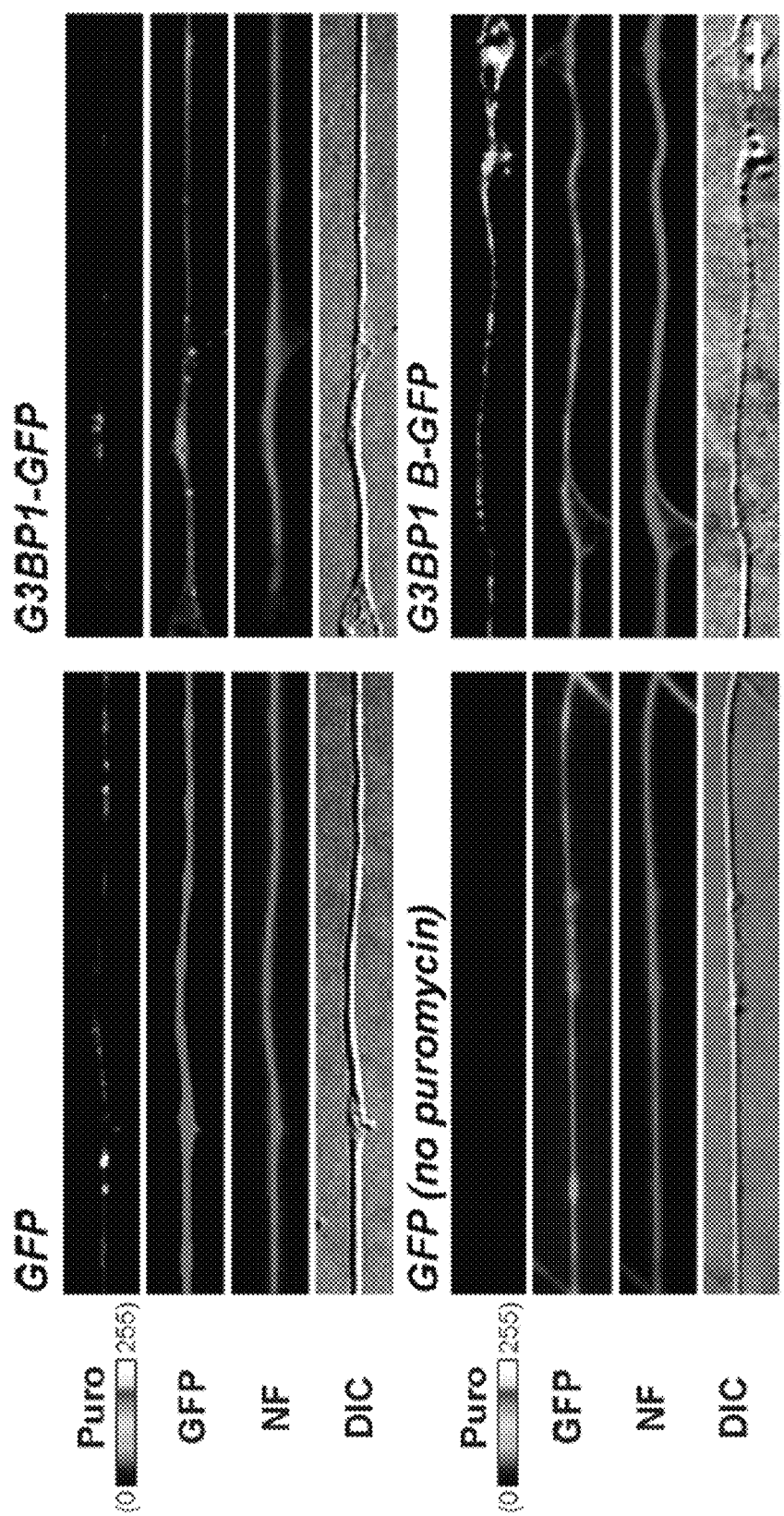
FIG. 12A show representative images for puromycin (Puro) incorporation in DRG neurons transfected with indicated constructs. Quantitation shows no change in cell body Puro signals (b), while the axons show a significant increase in Puro signals in the G3BP1 B domain expressing neurons (c) (N≥100 axons and N≥30 cell bodies over 3 repetitions; **p≤0.01 by one-way ANOVA with Tukey HSD posthoc) [scale bar=5 μm].
Figure 12B:
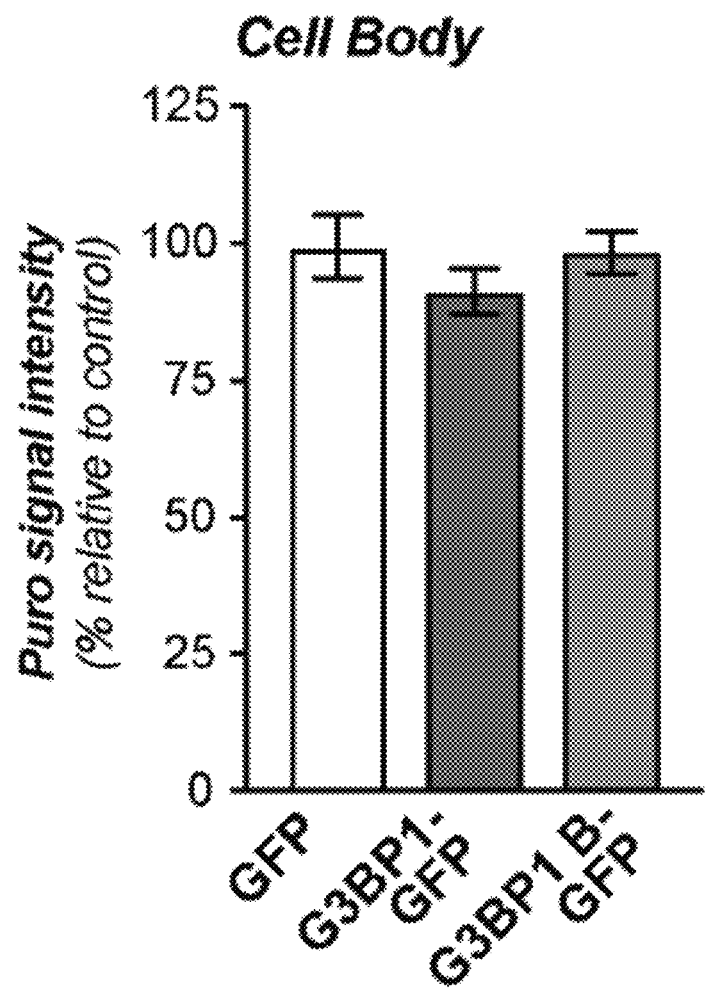
FIG. 12B shows quantitation that shows no change in cell body Puro signals.
Figure 12C:
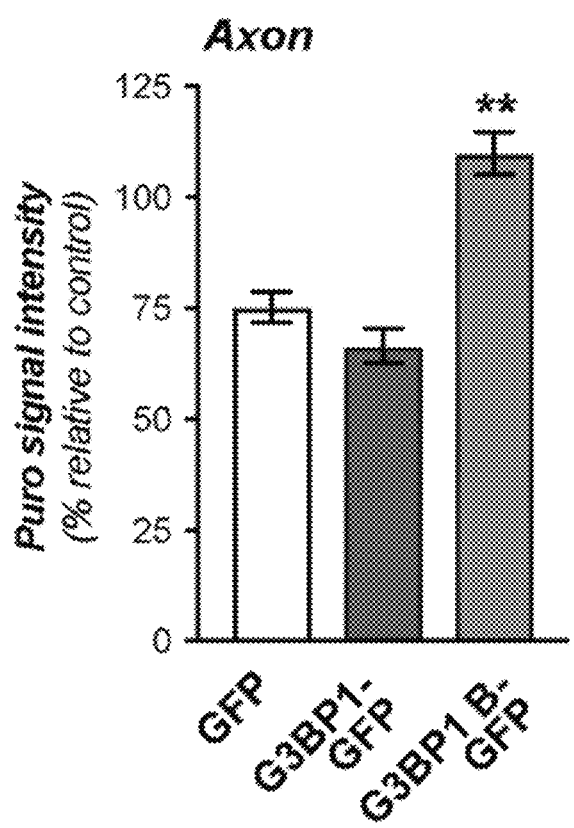
FIG. 12C shows that the axons show a significant increase in Puro signals in the G3BP1 B domain expressing neurons (c).
Figure 14B:
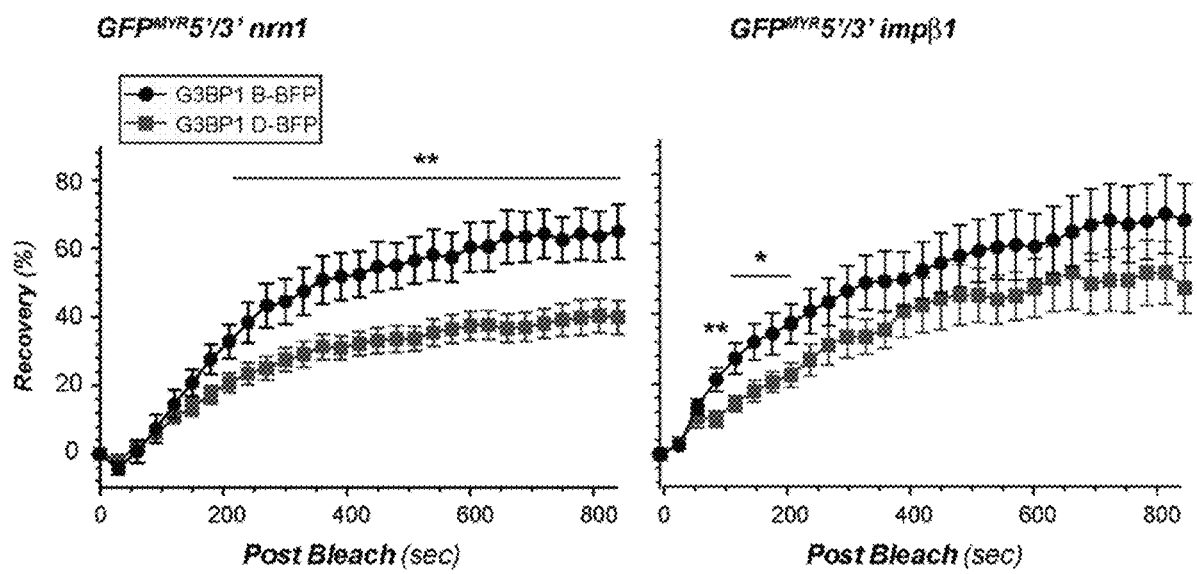
FIG. 14B shows FRAP analyses for DRGs expressing GFP$^{MYR}$5'/3'nrn1 or mGFP$^{MYR}$5'/3'impβ1 plus the G3BP1 B domain-BFP or G3BP1 D domain-BFP.
Figure 14C:
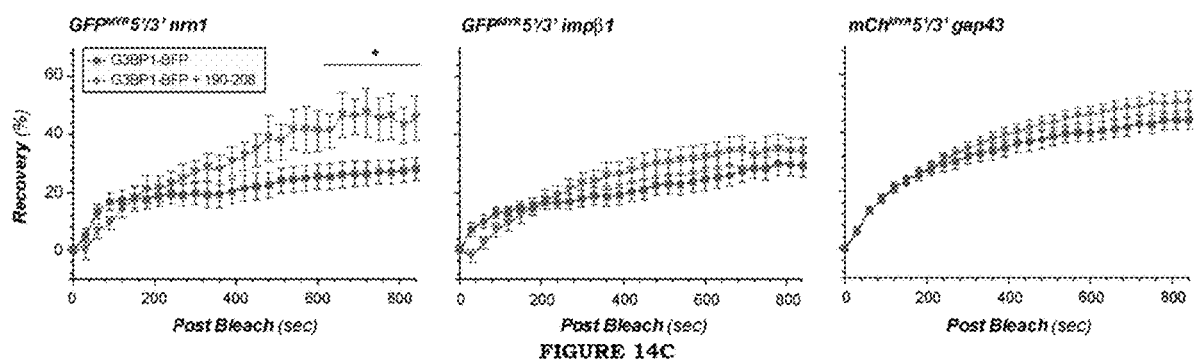
FIG. 14C shows FRAP analyses for DRGs expressing GFP$^{MYR}$5'/3'nrn1, GFP$^{MYR}$5'/3'impβ1, or mCh$^{MYR}$5'/3'gap43 plus G3BP1-BFP.
Figure 18A:
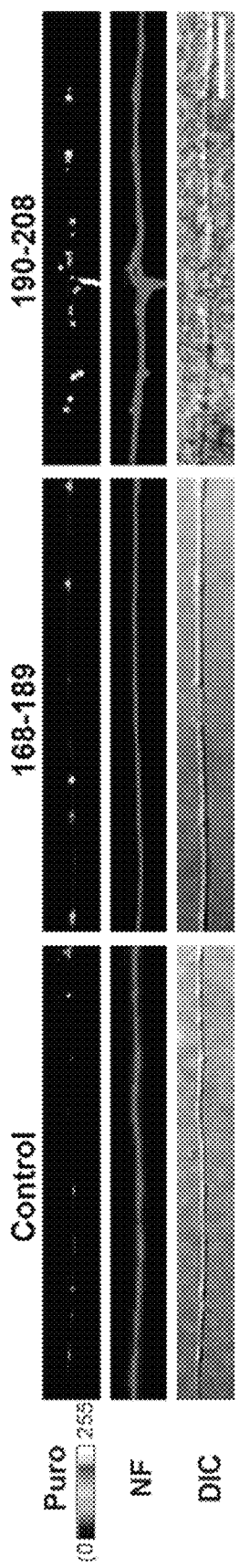
FIG. 18A shows representative images for puromycin (Puro) incorporation in DRG neurons treated with indicated peptides.

To determine if the exogenous G3BP1 B domain interrupts function of endogenous G3BP1, the current disclosure asked if expressing the B or D domains alters axonal mRNA translation. Intraaxonal translation of GFP$^{MYR}$5'/3'nrn1 was significantly higher in G3BP1 B domain expressing than in D domain expressing DRGs, but only modestly higher GFP$^{MYR}$5'/3'impβ1 translation was seen (FIG. 14B). Axonal mCh$^{MYR}$5'/3'gap43 translation showed no significant difference between B and D domain expressing neurons (FIG. 14A). The cell-permeable G3BP1 190-208 peptide also significantly rescued axonal translation of GFP$^{MYR}$573'nrn1 mRNA in G3BP1-overexpressing DRGs, but did not affect translation of GFP$^{MYR}$5'/3'impβ31 or mCh$^{MYR}$5'/3'gap43 mRNAs (FIG. 14C). Using a puromycinylation assay to test for translation of endogenous mRNAs, G3BP1 B domain expression led to significantly higher protein synthesis in axons but not cell bodies of cultured DRGs (FIGS. 12A, 12B, and 12C). Treatment with the cell-permeable G3BP1 190-208 peptide also increased axonal protein synthesis (FIG. 12D; FIG. 18A). Finally, the current disclosure directly tested if the interaction of endogenous mRNAs with G3BP1 is altered by B domain expression. Binding of Nrn1 and Impβ1 mRNAs to G3BP1-BFP was significantly decreased by B-domain expression, but GAP43 mRNA was not affected (FIG. 12E). Taken together, these data indicate that the growth-accelerating G3BP1 B domain and G3BP1 190-208 peptide can increase axonal protein synthesis.

Figure 18B:
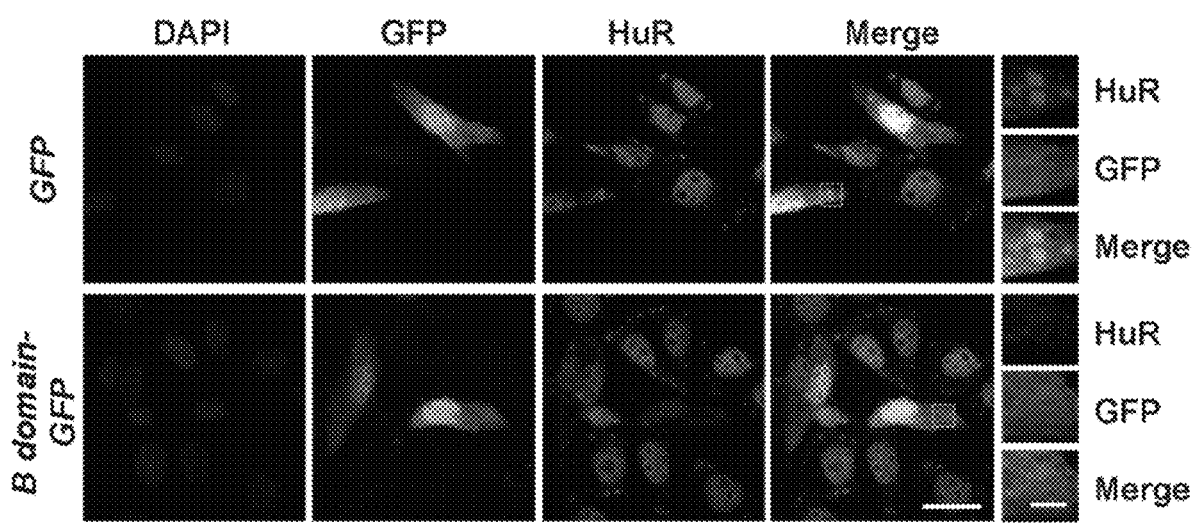
FIG. 18B shows representative images of HuR immunoreactivity in NIH-3T3 cells that were transfected GFP vs. G3BP1 B domain-GFP are shown after 30 min treatment with sodium arsenite (0.5 mM).
Figure 18C:
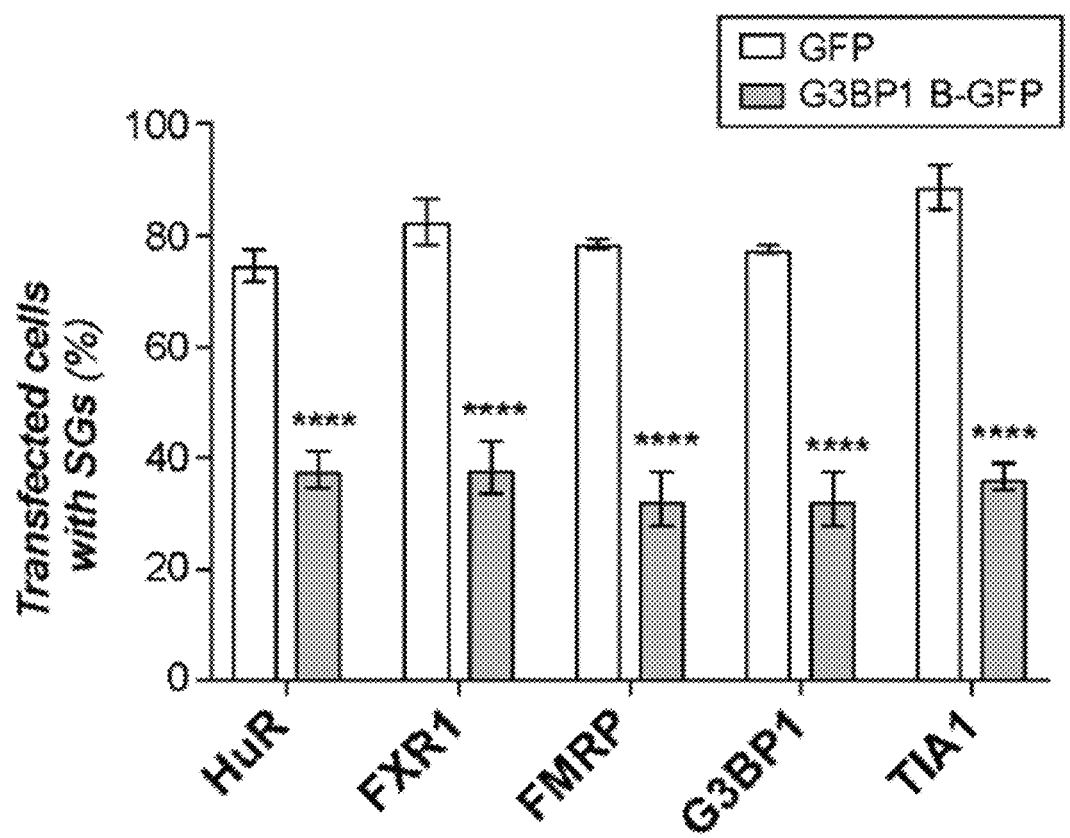
FIG. 18C shows quantification SGs in the transfected NIH-3T3 cells from FIG. 18A are shown based on the indicated immunostaining.

Considering the effects of the G3BP1 B domain and 190-208 peptide on axonal mRNA translation, the current disclosure reasoned that these agents might disrupt SGs. Indeed, G3BP1 B domain expression attenuated SG aggregation in NIH 3T3 cells exposed to sodium arsenite (FIGS. 18B and 18C), a potent inducer of SG aggregation. The current disclosure next used time-lapse imaging with DRG cultures to determine if the B domain affects the axonal SG-like structures, focusing on axons before and after addition of the cell-permeable 190-208 peptide. The 190-208 peptide caused a striking decrease in axonal G3BP1-mCh aggregates within 15 min (FIG. 5f-g). Moreover, the remaining SG-like structures in axons were significantly smaller after 190-208 peptide treatment (FIG. 5h), and the remaining aggregates showed greater motility than in control conditions).

DISCUSSION

Many studies have now documented mRNA translation in axons, and this is particularly prominent in the PNS where intra-axonal protein synthesis contributes to axon regeneration after injury. Some known SG proteins localize to axons, but intra-axonal functions for these proteins have not been extensively tested. The current disclosure's data indicates that blocking G3BP1's function in assembly of axonal SG-like structures increases intra-axonal protein synthesis and accelerates PNS axon regeneration. Thus, axonal G3BP1 is a negative modulator of intra-axonal protein synthesis and axon growth. With several thousand mRNAs identified in axons of cultured neurons, it is likely that translation of numerous axonal mRNAs will be regulated by G3BP1 as the current disclosure shows for Impβ1 and Nrn1 mRNAs. The colocalization of different mRNAs with these G3BP1 aggregates correlates with the growth status of neurons, and blocking G3BP1 aggregation provides a novel strategy to accelerate regeneration.

The difference between Impβ1 and Nrn1 colocalization with G3BP1 in naïve vs. injury conditioned neurons likely reflects different needs for the corresponding proteins in different growth states. Nrn1 protein promotes neurite growth, and increasing axonal targeting of Nrn1 mRNA increases axon growth in DRG neurons. Hence, the decrease in Nrn1 mRNA associated with SG-like aggregates in axons of injury-conditioned neurons would free the mRNA for translation to promote axon growth. On the other hand, Impβ1 mRNA translation is induced by axotomy, with its protein product providing a retrograde signal to activate regeneration-associated gene expression in the soma. Continued translation of Impβ1 mRNA likely decreases axon elongation due to its role in axon length sensing. Consequently, rapid axon growth after injury conditioning would be facilitated by sequestering Impβ1 mRNA from translation.

In summary, the current disclosure points to axonal G3BP1 as a modulator of intra-axonal protein synthesis and axon growth. Since G3BP1 is aggregated in uninjured PNS axons, the current disclosure's data points to unrealized functions for SG-like aggregates in axons under non-stress conditions. Preventing this SG-like aggregation of axonal proteins during regeneration increases the rate of axon regrowth. Considering that Tat fusion peptides for NR2B9c have been used in a clinical trial for ischemic protection during endovascular repair for intracranial aneurysms, the growth-promoting effects of the cell-permeable 190-208 G3BP1 peptide may represent a novel therapeutic lead for accelerating nerve regeneration. Since peripheral nerves typically regenerate at only 1-2 mm per day, accelerating axon growth rates by interfering with axonal G3BP1 function could significantly shorten recovery times and allow axons to reach a more receptive environment to reinnervate target tissues.

FIGURE LEGENDS

FIG. 8: G3BP1 localizes to axons in stress granule-like aggregates.

FIG. 8A, Immunofluorescence for G3BP1 shows signals in cell body (asterisk) and along distal neurites (arrows) in a cultured DRG neuron. Previous work has shown that neurites of these adult DRG neurons have axonal features and lack dendritic features; we will use 'axon' for describing these hereafter [scale bar=50 µm]. FIGS. 8B and 8C show single optical planes for axons of naïve DRG cultures co-labeled for G3BP1, HuR, FMRP and FXR1 or G3BP1, DCP1A and XRN1 are shown as indicated; boxed region represents the area higher magnification images are taken from (b). Axonal G3BP1 shows higher colocalization coefficients (c) for SG proteins than PB proteins (N≥30 axons over 3 repetitions) [scale bar=10 µm for large panels and 1 µm for small panels].

FIG. 9: G3BP1 is phosphorylated in regenerating axons.

FIG. 9A shows axons of DRG neurons transfected with indicated G3BP1 constructs vs. eGFP are shown. G3BP1-GFP and G3BP1$^{S149A}$-GFP show prominent aggregates in axons that colocalize with HuR (arrows). In contrast, axonal signals for G3BP1$^{S149E}$-GFP and eGFP appear more diffuse [Scale bar=5 µm]. FIG. 9B shows quantification of axonal aggregates for G3BP1-GFP, G3BP1$^{S149A}$-GFP, and G3BP1$^{S149E}$-GFP is shown as average±SEM (N≥10 neurons over 3 repetitions; p≤0.005 by one-way ANOVA with Tukey HSD post-hoc).

FIG. 9C shows FRAP analyses for neurons transfected with constructs as in A are shown as average normalized % recovery±SEM (see FIG. 13A for representative FRAP image sequences). G3BP1$^{S149A}$-GFP shows much lower recovery than G3BP1$^{S149E}$-GFP; G3BP1-GFP is intermediate between G3BP1$^{S149A}$-GFP and G3BP1$^{S149E}$-GFP (N≥13 axons over 3 repetitions; * p≤0.05 between G3BP1$^{S149A}$-GFP vs. G3BP1$^{S149E}$GFP by one-way ANOVA with Tukey HSD post-hoc). Only the 0-320 sec recovery signals for GFP are shown (at 840 sec GFP showed 85.5±4.7% recovery; p≤0.0001 vs. G3BP1$^{S149E}$-GFP by one-way ANOVA with Tukey HSD post-hoc).

FIGS. 9D and 9E shows exposure-matched confocal images for G3BP1$^{PS149}$ and NF are shown for sciatic nerve (d) as in FIG. 8D. There is a striking increase in G3BP1$^{PS149}$ signal in the regenerating axons. Quantification of these signals (e) shown as mean±SEM (N=3; * p≤0.05 by one-way ANOVA with Tukey HSD post-hoc) [scale bar=20 µm].

Figure 9F:
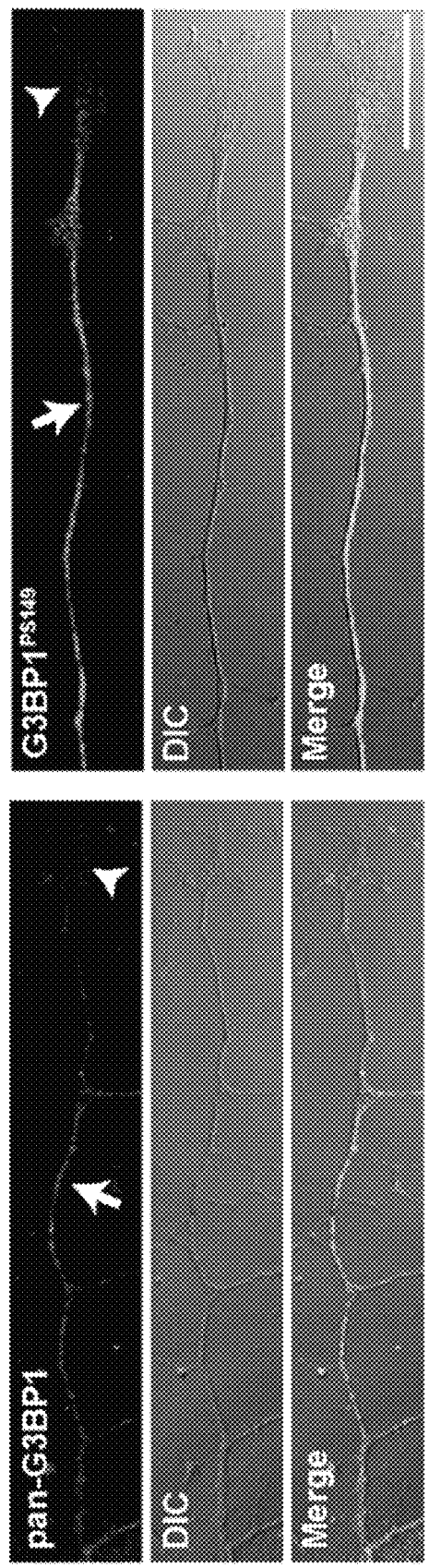
FIG. 9F shows distal axons of cultured DRGs immunostained with pan-G3BP1 vs. G3BP1$^{PS149}$ antibodies.
Figure 9G:
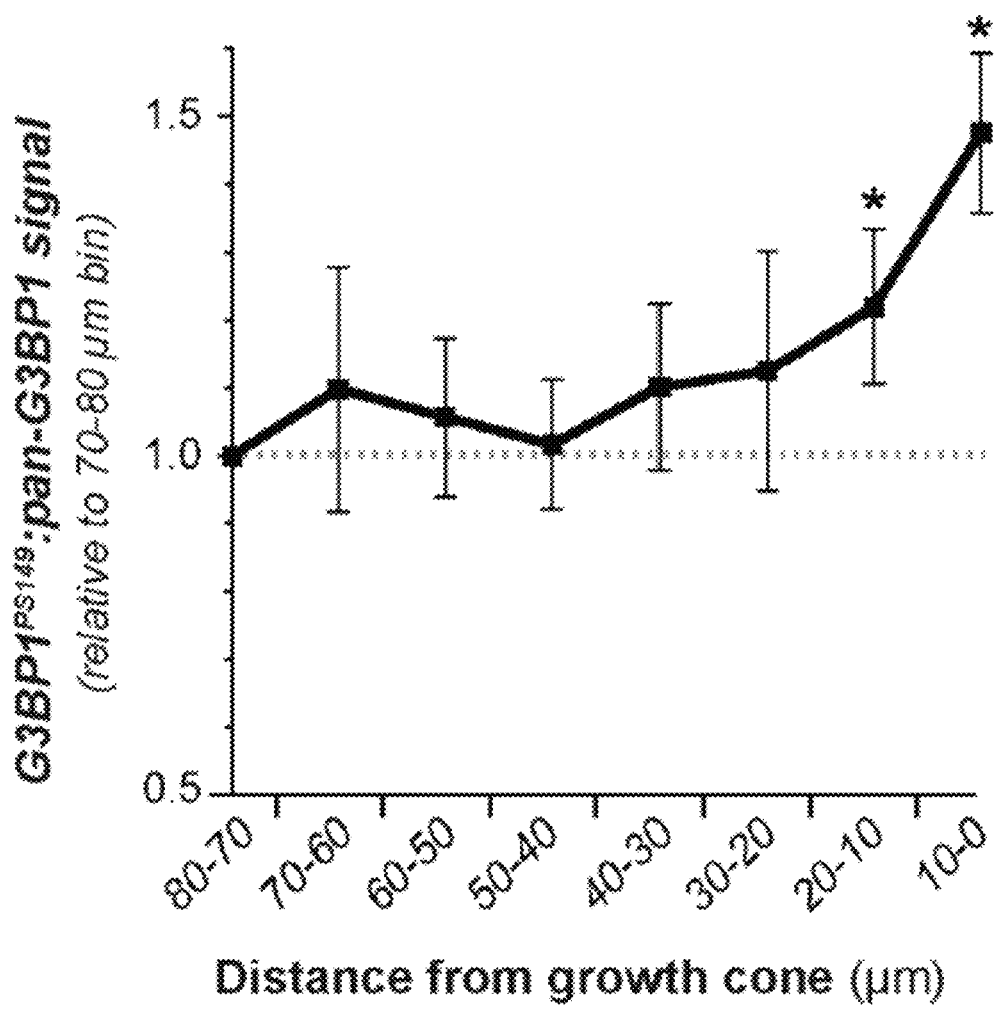
FIG. 9G shows quantification of the signals of FIG. 9F.

FIGS. 9F and 9G, shows distal axons of cultured DRGs immunostained with pan-G3BP1 vs. G3BP1$^{PS149}$ antibodies are shown as indicated (f). Aggregates of G3BP1 are visible in the axon shaft (arrow), but decrease moving distally towards the growth cone (arrowhead). G3BP1$^{PS149}$ signals are fairly consistent and extend into the growth cone (arrowhead). Quantification of signal (g) shows significant increase in ratio of G3BP1$^{PS149}$ immunoreactivity to G3BP1 aggregates moving distally to the growth cone (N≥9 neurons each over 3 repetitions; * p≤0.05 vs. 70-80 µm bin by one-way ANOVA with Tukey HSD post-hoc) [Scale bar=20 µm].

FIG. 10: G3BP1 regulates translation of axonal mRNAs.

FIG. 10A shows images of FISH/IF for indicated mRNAs and G3BP1 protein are shown for axons of naïve and 7 d injury-conditioned DRG neurons. Colocalization panel represents the mRNA:G3BP1 colocalization in a single optical plane [Scale bar=5 µm].

FIG. 10B shows quantification of colocalizations for Nrn1, Impβ1, and Gap43 mRNAs with G3BP1 in axons of neurons cultured from naïve or 7 d injury-conditioned animals shown as average Pearson's coefficient±SEM (N≥21 neurons over 3 repetitions;  p≤0.01 and * p≤0.005 by one-way ANOVA with Tukey HSD posthoc).

FIG. 10C shows schematics of translation reporter constructs used in panels d-f.

Figure 10D:
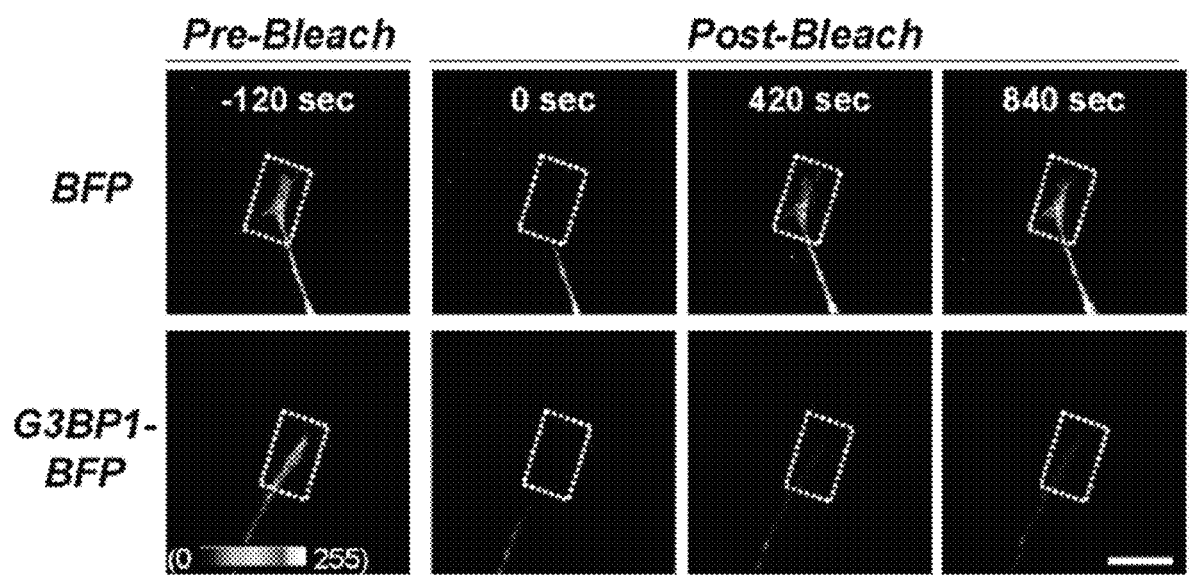
FIG. 10D shows representative FRAP image sequences for DRG neurons co-transfected with GFP$^{MYR}$5'/3'nrn1 plus BFP or G3BP1-BFP.
Figure 10E:
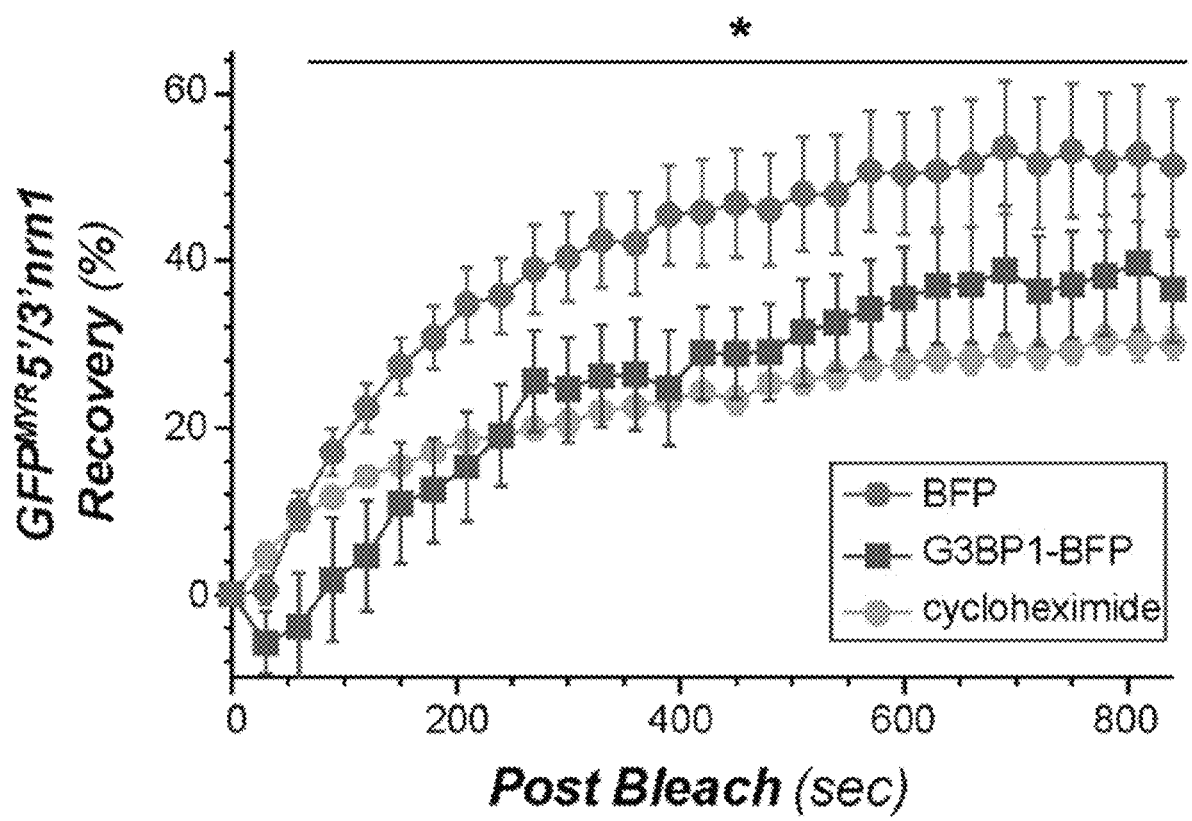
FIG. 10E shows quantifications of FRAP assays from DRGs expressing GFP$^{MYR}$5'/3'nrn1.
Figure 10F:
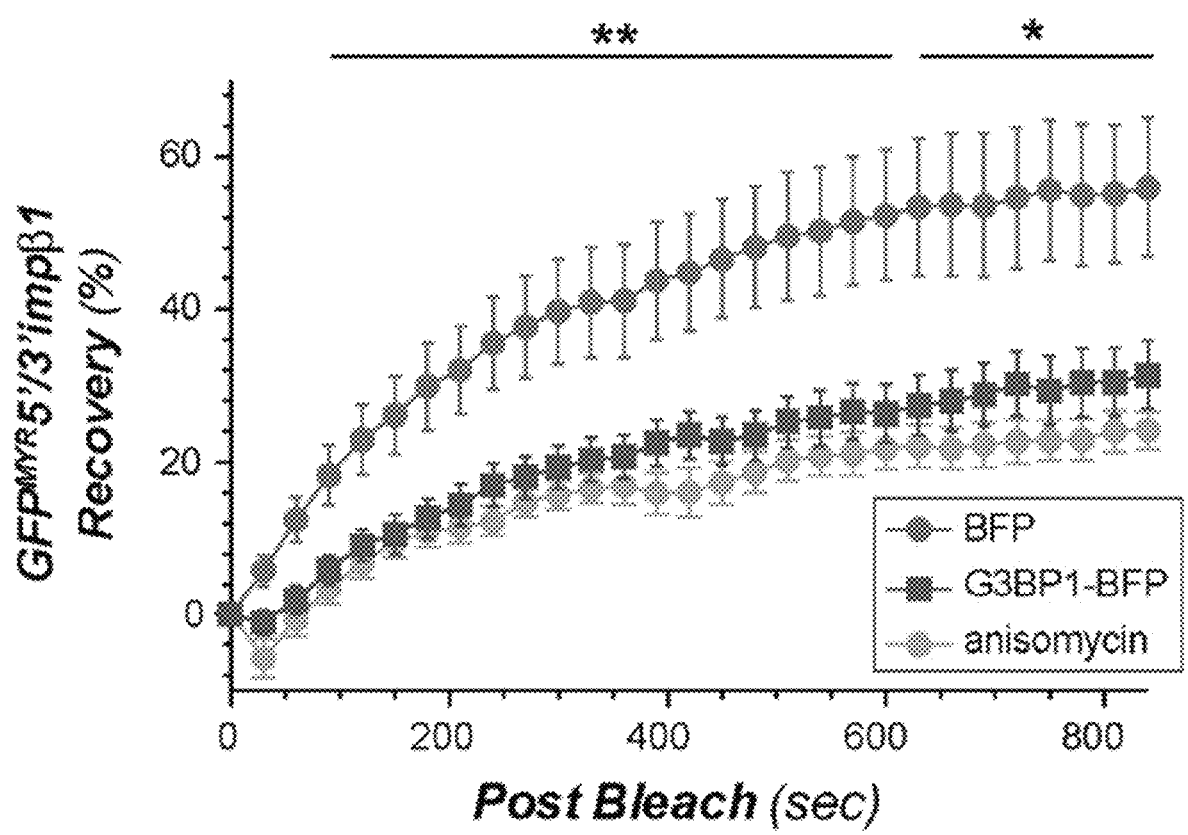
FIG. 10F shows quantifications of FRAP assays from DRGs expressing GFP$^{MYR}$5'/3'impβ1.
Figure 10G:
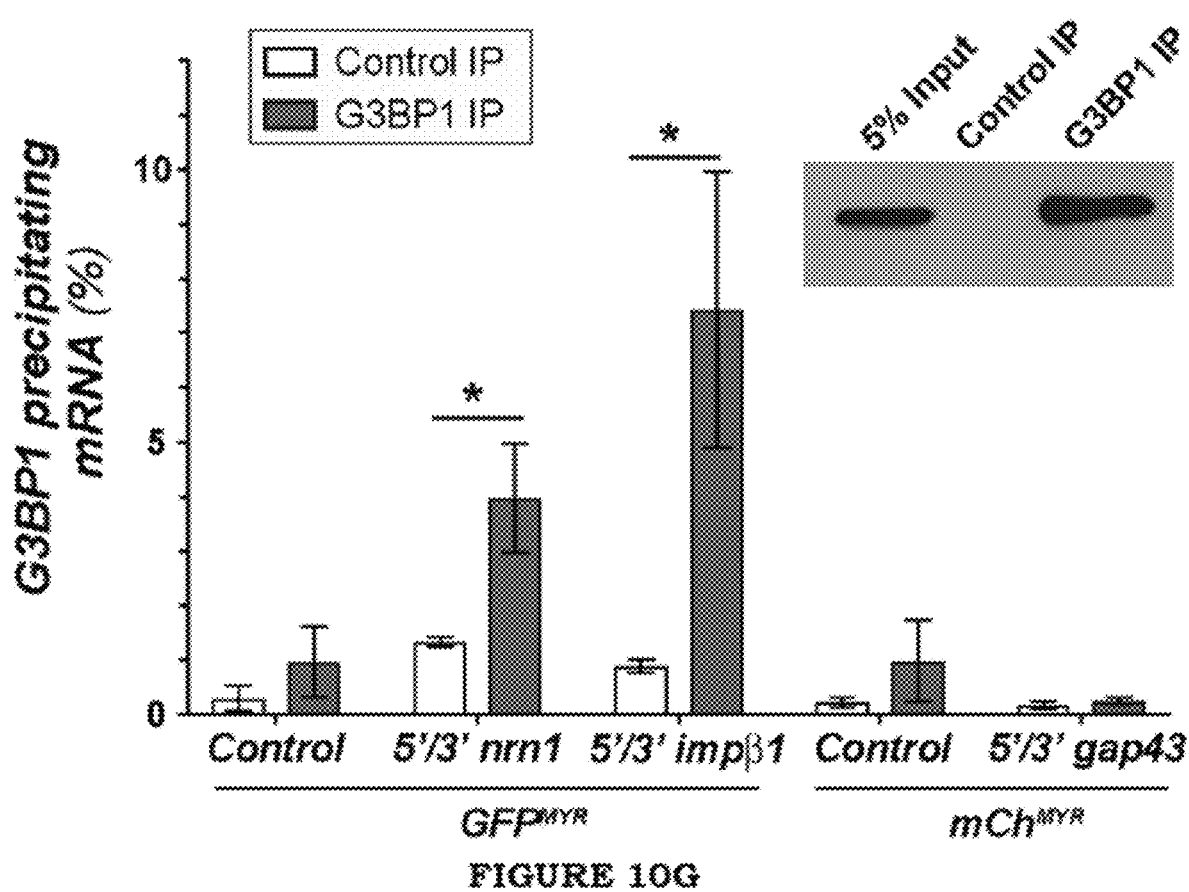
FIG. 10G shows HEK293T cells transfected with GFP$^{MYR}$5'/3'nrn1, GFP$^{MYR}$5'/3'impβ1 and mCh$^{MYR}$5'/3'gap43.

FIG. 10D shows representative FRAP image sequences for DRG neurons co-transfected with GFP$^{MYR}$5'/3'nrn1 plus BFP or G3BP1-BFP. Boxed regions represent the photobleached ROIs.

FIGS. 10E and 10F show quantifications of FRAP assays from DRGs expressing GFP$^{MYR}$5'/3'nrn1 (e) or GFP$^{MYR}$5'/3'impβ1 (f) translation reporters along with G3BP1-BFP or control BFP are shown as normalized, average % recovery±SEM (see FIG. 14A for mCh$^{MYR}$5'/3'gap43; N≥11 neurons over 3 repetitions; * p≤0.05, and ** p≤0.01 by one-way ANOVA with Tukey HSD post-hoc). Cultures treated with translational inhibitors showed reduced fluorescence recovery that paralleled G3BP1-overexpressing neurons.

FIG. 10G shows HEK293T cells transfected with GFP$^{MYR}$5'/3'nrn1, GFP$^{MYR}$5'/3' impβ1, and mCh$^{MYR}$5'/3'gap43 show significant enrichment of GFP$^{MYR}$5'/3'nrn1 and GFP$^{MYR}$5'/3' impβ1 mRNAs coimmunoprecipitating with G3BP1 immunoprecipitate vs. control. Western blot validating G3BP1 immunoprecipitation shown as inset. Values shown as average percent bound mRNA relative to input±SEM (N=4 culture preparations; * p≤0.05 by Student's t-test).

FIG. 11: G3BP1 acidic domain expression accelerates nerve regeneration.

FIG. 11A shows a schematic of G3BP1 domains as defined by Tourriere et al. (2003).

FIG. 11B shows representative images for NF-labeled DRG neurons transfected with indicated constructs. Images were acquired at 60 h post-transfection [scale bar=100 µm]. FIG. 17A shows axonal localization of these G3BP1-GFP domain proteins and FIG. 15A shows quantitation of axon growth from G3BP1 domain-expressing DRG neurons.

FIG. 11C shows quantitation of axon growth from DRGs (left) and cortical neurons (right) treated with cell-permeable 168-189 or 190-208 G3BP1 peptides. For DRGs, peptides were added to dissociated naïve or 7 d injury-conditioned DRGs at 12 h and axon growth was assessed at 36 h in vitro.

For cortical neurons, peptides were added to the axonal compartment of microfluidic devices at 3 d in vitro (DIV), and axon growth was assessed at 6 DIV. See FIG. 16C for images of cortical cultures (N≥95 over 3 DRG cultures and 9 microfluidic devices over 3 cultures; *** p≤0.005 by one-way ANOVA with Tukey HSD post-hoc).

FIG. 11D shows the extent of axon regeneration at 7 day post sciatic nerve crush in adult rats transduced with AAV5 encoding G3BP1-BFP, G3BP1 B domain-BFP, G3BP1 D domain-BFP, or GFP control as mean axonal profiles relative to crush site (0 mm)±SEM. For representative NF stained images see Extended Data S5B (N≥5 animals per condition; *=p≤0.05 and ****=p≤0.0001 by one-way ANOVA with Tukey HSD post-hoc).

FIG. 12: G3BP1 acidic domain increases axonal mRNA translation and disassembles stress granules.

FIGS. 12A, 12B, and 12C show representative images for puromycin (Puro) incorporation in DRG neurons transfected with indicated constructs are shown (a). Quantitation shows no change in cell body Puro signals (b), while the axons show a significant increase in Puro signals in the G3BP1 B domain expressing neurons (c) (N≥100 axons and N≥30 cell bodies over 3 repetitions; **p≤0.01 by one-way ANOVA with Tukey HSD posthoc) [scale bar=5 μm].

Figure 12D:
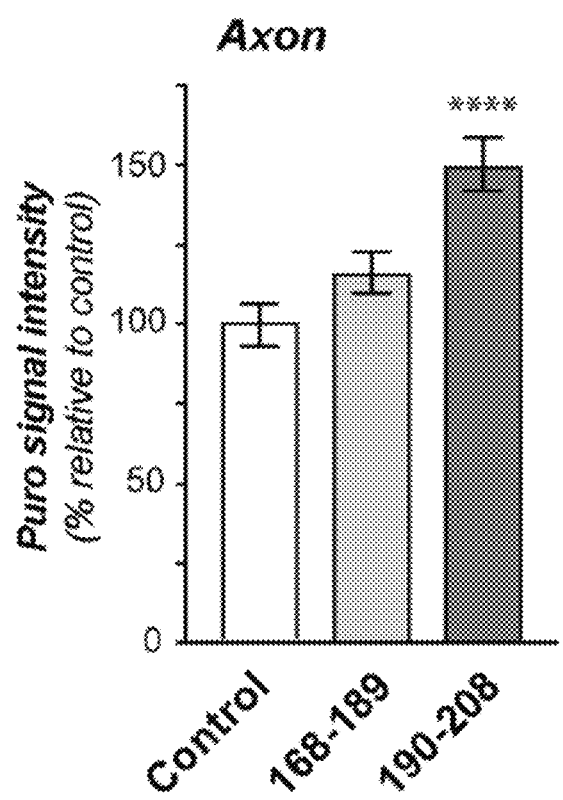
FIG. 12D show puro incorporation in DRG axons was also significantly increased by the 190-208 G3BP1 peptide treatment compared to control and 168-189 peptide exposure.
Figure 12E:
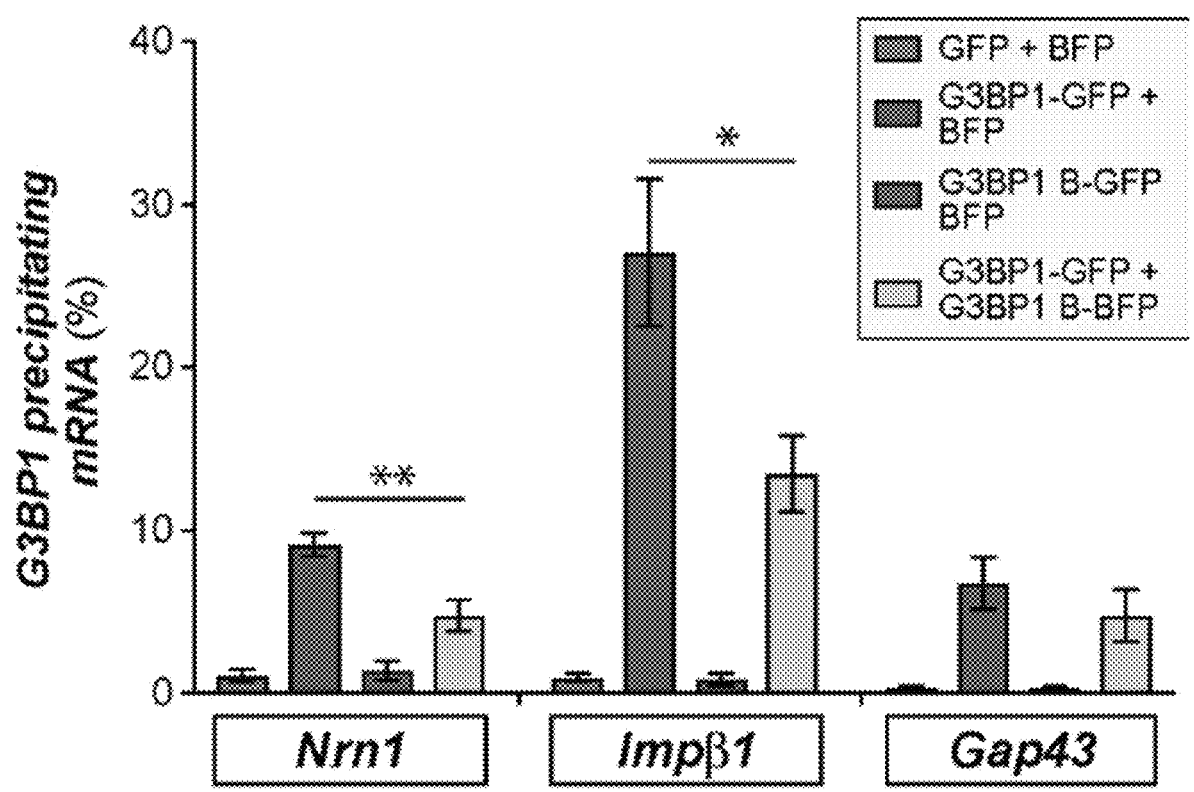
FIG. 12E shows RTddPCR for axonal mRNAs associated with G3BP1-GFP in DRG neurons as average % mRNA associated with G3BP1-GFP±SEM.

FIG. 12D show puro incorporation in DRG axons was also significantly increased by the 190-208 G3BP1 peptide treatment compared to control and 168-189 peptide exposure (N≥83 axons over 3 DRG cultures; ****p≤0.0001 by one-way ANOVA with Tukey HSD post-hoc). Representative images are shown in FIG. 18A.

FIG. 12E shows RTddPCR for axonal mRNAs associated with G3BP1-GFP in DRG neurons as average % mRNA associated with G3BP1-GFP±SEM. Nrn1 and Impβ1 mRNAs association with G3BP1-GFP significantly reduces by expression of B domain (N=4 culture preparations; * p≤0.05, ** p≤0.01 by Student's t-test).

Figure 12F:
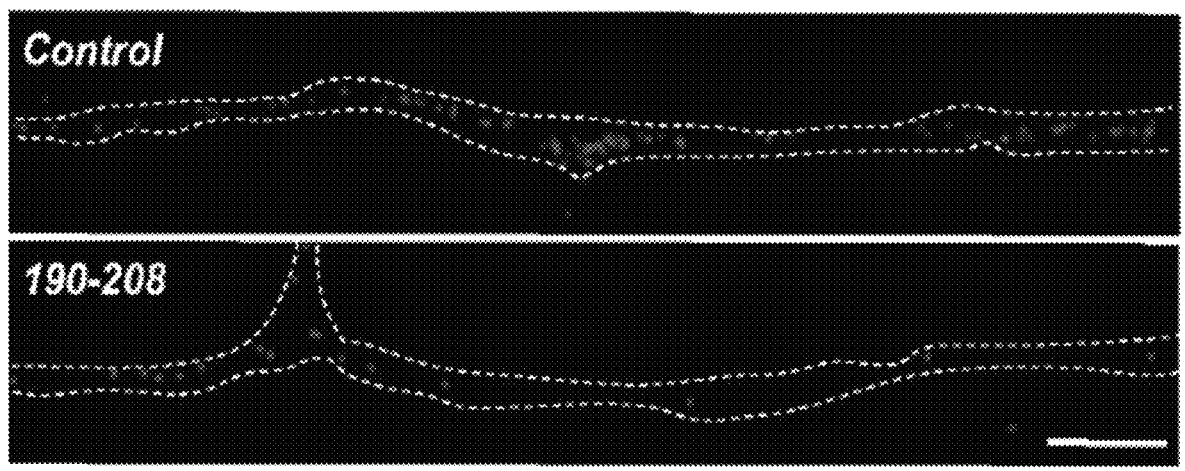
FIG. 12F show representative images of G3BP1-mCh in DRG axons±treatment with 190-208 G3BP1 peptide for 15 min.

FIG. 12F show representative images of G3BP1-mCh in DRG axons±treatment with 190-208 G3BP1 peptide for 15 min are shown. Axon tracing was generated from DIC images [scale bar=10 μm].

Figure 12G:
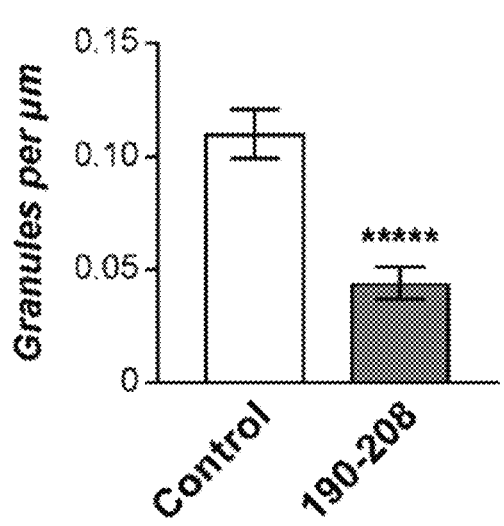
FIG. 12G show density of G3BP1-mCh aggregates along 100 μm length axons from DRG cultures treated as in FIG. 12F.

FIG. 12G show density of G3BP1-mCh aggregates along 100 μm length axons from DRG cultures treated as in FIG. 12F are shown (N≥51 axons over 3 repetitions; **** p≤0.0001 by Student's t-test).

Figure 12H:
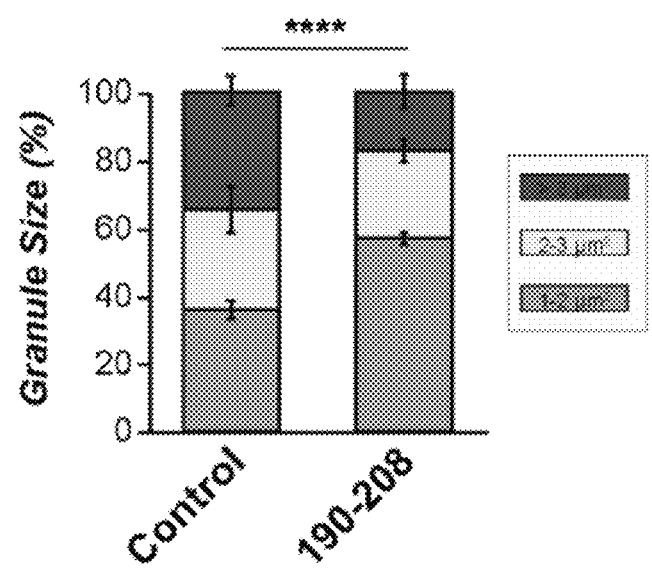
FIG. 12H shows the size of G3BP1-mCh aggregate as indicated bins for from DRG cultures treated as in FIG. 12F.

FIG. 12H size of G3BP1-mCh aggregate is shown as indicated bins for from DRG cultures treated as in FIG. 5f (N≥50 aggregates over 3 repetitions; **** p≤0.0001 for entire population distributions by Kolmogorov-Smirnov test).

Methods

Animal Use and Survival Surgery—

Institutional Animal Care and Use Committees of University of South Carolina, Emory University, and Weizmann Institute of Science approved all animal procedures. Male Sprague Dawley rats (175-250 g) were used for all sciatic nerve injury and DRG culture experiments. Embryonic day 18 (E18; male and female) rat pups were used for cortical neuron culture experiments. Isofluorane was used for anesthesia for AAV transduction and peripheral nerve injury.

For peripheral nerve injury, anesthetized rats were subjected to a sciatic nerve crush at midthigh as described. In cases where animals were transduced with virus prior to injury, AAV5 was injected into the proximal sciatic nerve 7 d prior to crush injury (at sciatic notch level; 9-14×10$^{10}$ particles in 0.6 M NaCl).

Axoplasm was obtained from sciatic nerve at 3, 7, 14, 21 and 28 d after crush injury at mid-thigh level. 2 cm segments of nerve proximal to the injury site (or equivalent level on contralateral [naïve] side) were dissected and axoplasm extruded into 20 mM HEPES [pH 7.3], 110 mM potassium acetate, and 5 mM magnesium acetate (nuclear transport buffer) supplemented with protease/phosphatase inhibitor cocktail (Roche) and RNasin Plus (Promega). After clearing by 20,000×g centrifugation at 4° C. for 30 min, supernatants were mixed with 3 volumes of Trizol LS (Invitrogen) for protein precipitation. 3 animals were used for each time point.

Cell Culture—

For primary neuronal cultures, L4-5 DRG were harvested in Hybernate-A medium (BrainBits) and then dissociated as known to those of skill in the art. After centrifugation and washing in DMEM/F12 (Life Technologies), cells were resuspended in DMEM/F12, 1×N1 supplement (Sigma), 10% fetal bovine serum (Hyclone), and 10 μM cytosine arabinoside (Sigma). Dissociated DRGs were plated immediately on laminin/poly-L-lysine-coated coverslips or transfected (see below) and then plated on coated coverslips.

For cortical neuron cultures, E18 cortices were dissected in Hibernate E (BrainBits) and dissociated using the Neural Tissue Dissociation kit (Miltenyi Biotec). For this, minced cortices were incubated in a pre-warmed enzyme mix at 37° C. for 15 min; tissues were then triturated and applied to a 40 μm cell strainer. After washing and centrifugation, neurons were seeded at a density of 1×105 cells per poly-D-lysine-coated microfluidic device (Xona Microfluidics). NbActive-1 medium (BrainBits) supplemented with 100 U/ml of Penicillin-Streptomycin (Life Technologies), 2 mM L-Glutamine (Life Technologies), and 1×N21 supplement (R&D Systems) was used as culture medium.

NIH-3T3 and HEK293T cells were maintained in DMEM (Life Technologies) supplemented with 10% FBS (Gibco) and 100 U/ml of Penicillin-Streptomycin (Life Technologies).

For DRG neuron transfection, dissociated ganglia were pelleted by centrifugation at 100×g for 5 min and resuspended in 'nucleofector solution' (Rat Neuron Nucleofector kit; Lonza). 5-7 μg plasmid was electroporated using an AMAXA Nucleofector apparatus (program SCN-8; Lonza). For siRNA transfection, 100 nM siRNAs (Dharmacon) were used with DharmaFECT 3 reagent and incubated for 36 h. G3BP1 siRNA sequence: 5' ccacauaggagcugggaauuu 3'. Non-targeting siRNAs (siCon) were as control. RTddPCR was used to test the efficiency of depletion (see below). HEK293T cells were transfected using Lipofectamine® 2000 per manufacturer's instructions (Invitrogen). AAV5 preparations were titrated in DRG cultures by incubating with 1.8-2.8×1010 particles of AAV5 overnight.

For arsenic treatment to induce SG aggregation, transfected NIH3T3 cells were grown to 60-80% confluence and were treated with 0.5 mM sodium arsenite (Sigma) for 30 min.

For peptide treatments, 10 μM Tat-fused peptides were added to dissociated DRG cultures at 2 or 12 h after plating. Neurite outgrowth was assessed 24 h after addition of peptides. For the cortical cultures, 10 μM peptide was applied to the axonal compartment at 3 d in vitro (DIV) and axonal growth was assessed at 6 DIV.

Plasmid and Viral Expression Constructs—

All fluorescent reporter constructs for analyses of RNA translation were based on eGFP with myristoylation element (GFP$^{MYR}$; originally provided by Dr. Erin Schuman, Max-Plank Inst., Frankfurt) or mCherry plasmid with myristoylation element (mCh$^{MYR}$). Reporter constructs containing 5' and 3'UTRs of rat Nrn1 and Gap43 mRNAs have been published. For Impβ1, the 5'UTR was cloned by PCR and inserted directly upstream of the initiation codon in GFP$^{MYR}$3'impβ1 (includes 3'UTR of rat Impβ1 mRNA).

Human G3BP1 wild type, S149A, S149E and deletion constructs as GFP-tagged proteins were generously provided by Dr. Jamal Tazi, Institut de Génétique Moléculaire de Montpellier. The G3BP1-mCherry construct was generated by PCR, amplifying G3BP1 CDS with 5' NheI and 3' HindIII restriction sites. After NheI+HindIII digestion, G3BP1 CDS was subcloned into NheI+HindIII-digested pmCherry-N1 vector (Clontech).

AAV5 preparations were generated in UNC Chapel Hill Viral Vector Core. All plasmid inserts were fully sequenced prior to generating AAV. BglII+XhoI digested human G3BP1 cDNA (from pGFPG3BP1) was subcloned into BamHI+XhoI digested pAAV-cDNA6-V5His vector (Vector Biolabs). G3BP1 deletion constructs were amplified by PCR with terminal HindIII and XhoI restriction sites (primer sequences available on request). After digestion with HindIII and XhoI, products were cloned into HindIII+XhoI-digested pAAV-cDNA6-V5His vector. BFP was excised from the pTagBFP-N vector (Evrogen) using EcoRI+NotI and ligated in-frame directly 3' of the G3BP1 sequences in pAAV-cDNA6-V5His.

Generation of Tat-tagged G3BP1 B domain peptides—

Three peptides were generated from the rat G3BP1 B domain sequence (amino acids 140-220; UniProt ID # D3ZYS7 RAT) by Bachem Americas, Inc. Peptides were synthesized with N-terminal dansyl chloride or FITC and N- or C-terminal HIV Tat peptide for cell permeability; the Tat sequence was placed at the least conserved end of the sequence based on P-BLAST of sequences available in UniProt database. Peptide sequences with Tat sequence were (Tat shown in italics): 147-166, SEQ ID NO: 13 SEQ ID NO: 13 Glu Glu Ser Glu Glu Glu Val Glu Glu Pro Glu Glu *Arg Gln Gln Ser Pro Glu Val Val Tyr Gly Asn Lys Lys Asn Asn Gln Asn Asn Asn*; 168-189, SEQ ID NO: 14 Am Asp Ser Gly Thr Phe Tyr Asp Gln Thr Val Ser Asn Asn Leu Glu Glu His Leu Glu Glu Pro *Tyr Gly Asn Lys Lys Asn Asn Gln Asn Asn Asn*; and 190-208, SEQ ID NO: 15 *Tyr Gly Asn Lys Lys Asn Asn Gln Asn Asn Asn* Val Val Glu Pro Glu Pro Glu Pro Glu Pro Glu Pro Glu Pro Val Ser.

Immunofluorescent Staining—

All procedures were performed at room temperature (RT) unless specified otherwise. Cultured neurons were fixed in 4% paraformaldehyde (PFA) in phosphate-buffered saline (PBS) and processed as described. Primary antibodies consisted of: rabbit anti-G3BP1 (1:200, Sigma), RT97 mouse anti-neurofilament (NF; 1:500, Devel. Studies Hybridoma Bank), and rabbit anti-G3BP1$^{PS149}$ (1:300, Sigma). FITC-conjugated donkey anti-rabbit and Cy3-conjugated donkey anti-mouse (both at 1:200, Jackson ImmunoRes.) were used as secondary antibodies.

For G3BP1 colocalization with SG and PB proteins, Zenon antibody labeling kit (Life Technologies) was used to directly label antibodies with fluorophores. Combinations of rabbit anti-G3BP1 (Sigma)+Alexa-488, rabbit anti-HuR (Millipore)+Alexa-405, rabbit anti-FMRP (Cell Signaling Tech)+Alexa-555, and rabbit anti-FXR1 (kind gift from Dr. Khandjian, Institut Universitaire en Santé Mentale de Québec)+Alexa-633 or rabbit anti-G3BP1+Alexa-488, rabbit anti-DCP1A (Abcam)+Alexa-405, and rabbit anti-XRN1 (Bethyl Lab)+Alexa-633 were used at 1:50 dilution for each antibody. Equal amounts of rabbit-IgG labeled with Alexa-405, -488, -555 and -633 were used as control.

For quantifying axonal content of G3BP1 and G3BP1$^{PS149}$ in peripheral nerve, sciatic nerve segments were fixed for 4 h in 4% PFA and then cryoprotected overnight in 30% sucrose, PBS at 4° C. 10 µm cryostat sections were processed for immunostaining as previously described6. Primary antibodies consisted of rabbit anti-G3BP1 (1:100), rabbit anti-phospho-G3BP1PS149 (1:100), and RT97 mouse anti-NF (1:300). Secondary antibodies were FITC-conjugated donkey anti-rabbit and Cy3-conjugated donkey anti-mouse (both at 1:200, Jackson ImmunoRes.). Immunoblotting confirmed the specificity of the anti-G3BP1 and -G3BP1PS149 antibodies.

Paraffin sections were used for analyses of nerve regeneration. For this, 10 µm thick paraffin sections of sciatic nerve were deparaffinized in 100% xylene (2×10 min) followed by 100% ethanol (2×10 min). Sections were rehydrated by sequential incubations in 95, 75 and 50% ethanol for 5 min each, and then rinsed in deionized water. Sections were permeabilized in 0.3% Triton X-100 in PBS, and then rinsed in PBS for 20 min and equilibrated in 50 mM Tris [pH 7.4], 150 mM NaCl, 1% heat-shock bovine serum albumin (BSA), and 1% protease-free BSA (Roche) ('IF buffer'). Sections were then blocked in IF buffer plus 2% heat-shock BSA, and 2% fetal bovine serum for 1.5-2 h. After blocking, samples were incubated overnight at 4° C. in humidified chamber with the primary antibodies in IF buffer. Samples were washed in IF buffer three times and then incubated in secondary antibodies diluted in IF buffer for 45 min. Samples were washed in IF buffer three times followed by rinse in PBS and deionized water. Primary antibodies consisted of: RT97 mouse anti-NF (1:300) and rabbit anti-RFP (1:100, Rockland Immun. Chem.). The RFP antibody was confirmed to detect BFP by immunoblotting (see below) and immunolabeling of transfected DRG neurons (data not shown). Secondary antibodies were used as above.

All samples were mounted with Prolong Gold Antifade (Invitrogen) and analyzed by epifluorescent or confocal microscopy. Leica DMI6000 epifluorescent microscope with ORCA Flash ER CCD camera (Hamamatsu) or Leica SP8X confocal microscope with HyD detectors was used for imaging unless specified otherwise. For quantitation between samples, imaging parameters were matched for exposure, gain, offset and post-processing.

Fluorescence In-Situ Hybridization (FISH)—

For FISH, DRG cultures were fixed for 15 min in 2% PFA in PBS. RNA-protein colocalization was performed using custom 5' Cy3-labeled 'Stellaris' probes (probe sequences available upon request; Biosearch Tech.). Scrambled probes were used as control for specificity; samples processed without addition of primary antibody were used as control for antibody specificity. Primary antibodies consisted of rabbit anti-G3BP1 (1:100) and RT97 mouse anti-NF (1:200). FITC-conjugated donkey anti-rabbit and Cy5-conjugated donkey anti-mouse (both at 1:200) were used as secondaries. Samples were mounted as above and analyzed using a Leica SP8X confocal microscope. Samples were post-processed with Huygens deconvolution integrated into the Leica LSM software and analyzed as outlined below for RNA-protein colocalization.

Fluorescence Recovery after Photobleaching (FRAP)—

FRAP was used to test for axonal mRNA protein synthesis using diffusion-limited GFP$^{MYR}$ and mCherry$^{MYR}$ reporters as described with minor modifications. In each case, DRG neurons were co-transfected with GFP$^{MYR}$5'/3'nrn1+mCherry$^{MYR}$5'/3'gap43 or GFP$^{MYR}$5'/3'impβ1+mCherry$^{MYR}$5'/3'gap43 so that recovery of both reporters could be analyzed simultaneously. Cells were maintained at 37° C., 5% CO2 during imaging sequences. 488 nm and 514 nm laser lines on Leica SP8X confocal microscope were used to bleach GFP and mCherry signals, respectively (Argon laser at 70% power, pulsed every 0.82 sec for 80 frames). Pinhole was set to 3 Airy units to ensure full thickness bleaching and acquisition (63×/1.4 NA oil immersion objective). Prior to photobleaching, neurons were imaged every 60 sec for 2 min to acquire baseline fluorescence the region of interest (ROI; 15% laser power, 498-530 nm for GFP and 565-597 nm for mCherry emissions, respectively). The same excitation and emission parameters were used to assess recovery over 15 min post-bleach with images acquired at 30 sec intervals. To determine if fluorescence recovery in axons was from translation, cultures were treated with 150 µg/ml cycloheximide (Sigma) or 100 µM anisomycin (Sigma) for 30 min. prior to photobleaching for $GFP^{MYR}5'/3'nrn1+mCherry^{MYR}5'/3'gap43$ and $GFP^{MYR}5'/3'impβ1+mCh^{MYR}5'/3'gap43$ transfected DRGs, respectively. For peptide treatments, G3BP1-mCh transfected DRG neurons were treated with 10 µM G3BP1 peptides after acquiring the baseline expression values. Photobleaching followed by analyses of recovery was performed after 30 min of peptide exposure.

For testing G3BP1 protein mobility in axons, DRG neurons were transfected with $G3BP1^{S149A}$-GFP or $G3BP1^{S149E}$-GFP and imaged as above but only the 488 nm laser was used for photobleaching (Argon laser at 70% power, pulsed every 0.82 sec for 80 frames).

Fluorescent intensities in the ROIs were calculated by the Leica LASX software. For normalizing across experiments, fluorescence intensity value at t=0 min post-bleach from each image sequence was set as 0%. The percentage of fluorescence recovery at each time point after photobleaching was then calculated by normalizing relative to the pre-bleach fluorescence intensity (set at 100%).

Live Cell Imaging for G3BP1-mCherry Granules—

DRG neurons were transfected with G3BP1-mCherry, and 36 h later distal axons were imaged using Leica SP8X confocal microscope with environmental chamber maintained at 37° C., 5% CO2 (with 63×/1.4 NA oil immersion objective). Confocal pinhole was set to 0.43 airy units. G3BP1-mCherry signals were imaged in axon shaft every 2 sec for 100 frames (at 540 nm excitation and 23% white light laser power; 565-597 nm emission). To study the effect of the G3BP1 190-208 peptide on the G3BP1-mCherry granules, 10 µM FITC-conjugated peptide was added to the media and 15 min later imaging was continued.

For G3BP1-mCherry aggregates, a 100 µm of the axon shaft was considered (≥200 µm from cell body). Thresholding was applied to acquired image sequences using ImageJ to generate binary masks. ImageJ particle analyzer was used for analysis. G3BP1 aggregates with area of ≥1 µm2 were considered as SG-like structures. For analyzing the G3BP1 aggregate velocity, ImageJ Trackmate plug-in was used.

Puromycinylation Assay—

To visualize newly synthesized proteins in cultured neurons, the current disclosure used the Click-iT® Plus OPP Protein Synthesis Assay Kit per manufacturer's instructions (Invitrogen/Life Technologies). Briefly, 3 DIV cultures were incubated with 20 µM O-propargyl-puromycin (OPP) for 30 min at 37° C. OPP-labeled proteins were detected by cross-linking with Alexa Fluor-594 picolyl azide molecule. Coverslips were then mounted with Prolong Gold Antifade (Invitrogen) and imaged with Leica DMI6000 epifluorescent microscope as above. ImageJ was used to quantify the Puromycinylation signals in distal axons and cell bodies.

Immunoblotting—

For immunoblotting, protein lysates or immunoprecipitates were denatured by boiling in Laemmle sample buffer, fractionated by SDS-PAGE, and transferred to nitrocellulose membranes. Blots were blocked for 1 h at room temperature with 5% non-fat dry milk in Tris-buffered saline with 0.1% Tween 20 (TBST) for anti-GFP, -tagBFP, and -G3BP1 antibodies; 5% BSA in TBST was used for blocking anti-$G3BP1^{PS149}$ antibody. Primary antibodies diluted in appropriate blocking buffer were added to the membranes and incubated overnight incubation at 4° C. with rocking. Primary antibodies consisted of: rabbit anti-G3BP1 (1:2,000; Sigma), rabbit anti-G3BP1PS149 (1:1,000; Sigma), rabbit anti-GFP (1:5,000; Abcam), rabbit anti-TagBFP (1:4,000; Evrogen). After washing in TBST, blots were incubated HRP-conjugated anti-rabbit IgG antibodies (1:5,000; Jackson lab) diluted in blocking buffer for 1 h at room temperature. After washing signals were detected using ECL Prime™ (GE Healthcare).

RNA Immunoprecipitation (RIP)—

HEK293T cells or DRG neurons were lysed in 100 mM KCl, 5 mM $MgCl^2$, 10 mM HEPES [pH 7.4], 1 mM DTT, and 0.5% NP-40 (RIP buffer) supplemented with 1× protease inhibitor cocktail (Roche) and RNasin Plus (Invitrogen). Cells were passed through 25 Ga needle 5-7 times and cleared by centrifugation at 12,000×g for 20 min. Cleared lysates were pre-absorbed with Protein A-Dynabeads (Invitrogen) for 30 min. Supernatants were then incubated with primary antibodies for 3 h and then immunocomplexes precipitated with Protein G-Dynabeads (Invitrogen) for additional 2 h at 4° C. with rotation. Mouse anti-G3BP1 (5 µg, BD Biosciences) and rabbit anti-GFP (5 µg, Abcam) antibodies were used for immunoprecipitation. Beads were washed 6 times with cold RIP buffer. Bound RNAs were purified and analyzed by RTddPCR (see below).

RNA isolation and PCR analyses—

RNA was isolated from immunoprecipitates and cultures using the RNeasy Microisolation kit (Qiagen). Fluorimetry with Ribogreen (Invitrogen) was used for RNA quantification. For analyses of total RNA levels and inputs for RIP analyses, RNA yields were normalized across samples prior to reverse transcription using Sensifast (Bioline). For RIP assays, an equal proportion of each RIP was used for reverse transcription with Sensifast. ddPCR products were detected using Evagreen or Taqman primer and probe sets (Biorad or Integrated DNA Tech; sequences available on request) and QX200™ droplet reader (Biorad). In GFP RIP experiment, B domain-BFP expression consistently increased G3BP1-GFP levels in the DRG neurons. So the level of mRNA precipitating with G3BP1-GFP was normalized to the G3BP1-GFP signals from immunoblotting across each sample in each experiment.

Image Analyses and Processing—

For protein-protein and protein-mRNA colocalization, xyz scan sequence captured 100 µm segments of axon shaft (separated from cell body and growth cone by ≥200 µm) were deconvolved using Huygens Hyvolution software. Colocalization was analyzed using ImageJ JACoP plug-in (https://imagej.nih.gov/ij/plugins/track/jacop.html) to calculate Pearson's coefficient. These coefficient calculations were independently validated with Volocity software (Perkin Elmer).

For analyses of protein levels in tissues, z planes of the xyz tile scans from 3-5 locations along each nerve section were analyzed using ImageJ. Colocalization plug-in was used to extract protein signals that overlap with axonal marker (NF) in each plane, with the extracted 'axon-only' signal projected as a separate channel. For calculating axonal G3BP1 aggregate and $G3BP1^{PS149}$ signal intensities, absolute signal intensity was quantified in each xy plane of the 'Colocalization' extracted images for axonal only G3BP1 and G3BP1$^{PS149}$ using ImageJ. Protein signal intensities across the individual xy planes were then normalized to NF immunoreactivity area. The relative protein signal intensity was averaged for all image locations in each biological replicate.

For neurite outgrowth, images from 60 h DRG cultures were analyzed for neurite outgrowth using WIS-Neuromath. Axon morphology was visualized using GFP and/or NF immunofluorescence as described.

To assess regeneration in vivo, tile scans of NF-stained nerve sections were post-processed by Straighten plug-in for ImageJ (http://imagej.nih.gov/ij/). NF positive axon profiles were then counted in 30 μm bins at 0.3 mm intervals distal from crush site. Number of axon profiles present in the proximal crush site was treated as the baseline, and values from the distal bins were normalized to this to calculate the percentage of regenerating axons.

Statistical Analyses—

Kaleidagraph (Synergy) or Prism (GraphPad) software packages were used for statistical analyses. One-way ANOVA was used to compare means of independent groups and Student's t-test was used to compare smaller sample sizes of the in vivo analyses. p values of ≤0.05 were considered as statistically significant.

Figure 19:
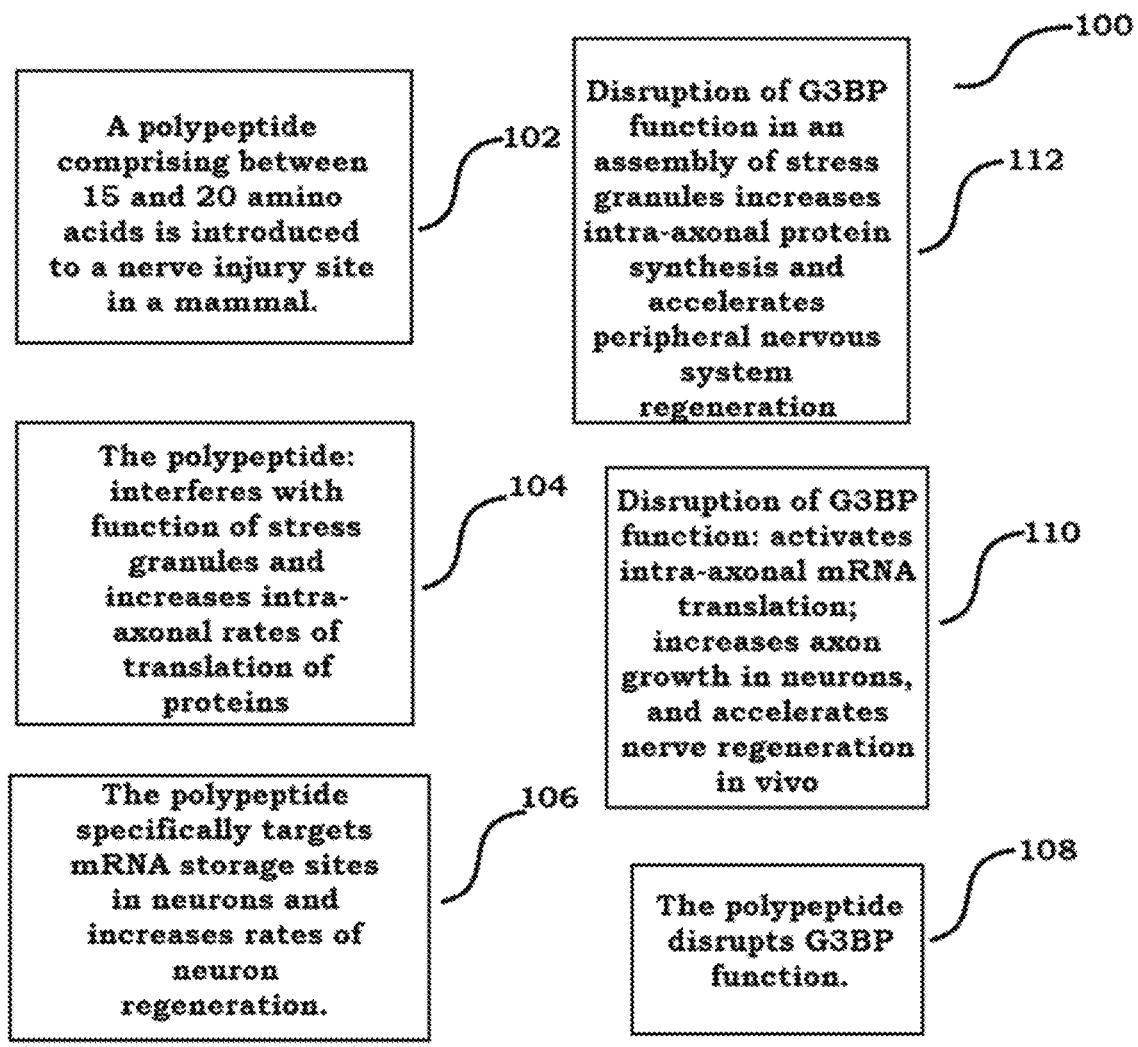
FIG. 19 shows one embodiment of a method of the current disclosure.

In one embodiment, see FIG. 19, a method 100 for treating nerve injury in a mammal may be provided. At step 102, a polypeptide comprising between 15 and 20 amino acids may be introduced to a nerve injury site in the mammal. At step 104, the polypeptide may interfere with function of stress granules and increase intra-axonal rates of translation of proteins needed for nerve regeneration. The polypeptide may have an amino acid sequence set as forth in SEQ ID NO. 2. At step 106, the polypeptide may specifically target mRNA storage sites in neurons and increases rates of neuron regeneration. At step 108, the polypeptide may disrupt G3BP functions. At step 110, disruption of G3BP functions may: activate, intra-axonal mRNA translation; increase axon growth in neurons; and accelerate nerve regeneration in vivo. Disruption of G3BP functions may be accomplished via siRNA-mediated knockdown of G3BP1. At step 112, disrupting G3BP1's function in an assembly of axonal stress granule structures may increases intra-axonal protein synthesis and accelerates peripheral nervous system axon regeneration. Accelerated axon growth regeneration may be facilitated by sequestering Impβ1 mRNA from translation.

Figure 20:
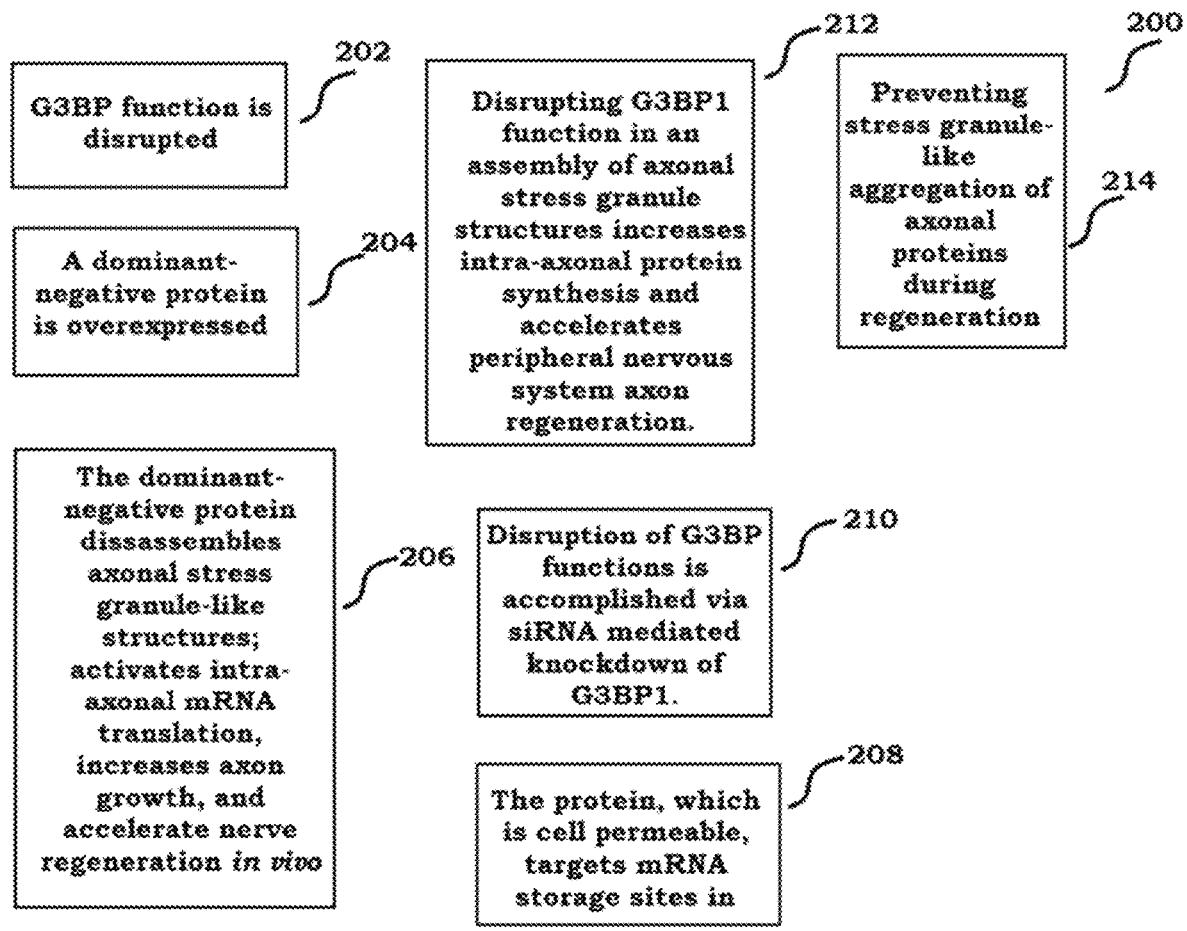
FIG. 20 shows one embodiment of an alternative method of the current disclosure.

FIG. 20 shows an alternative method 200 wherein. At step 202, G3BP function may be disrupted. At step 204, a dominant-negative protein may be overexpressed. At step 206, the dominant-negative protein may disassemble axonal stress granule-like structures, activate intra-axonal mRNA translation, increase axon growth in neurons; and accelerate nerve regeneration in vivo. The protein may comprise between 15 and 20 amino acids and may have an amino acid sequence as set forth in SEQ ID NO: 2. At step 208, the protein is cell permeable and targets mRNA storage sites in neurons. At step 210, disruption of G3BP functions may be accomplished via siRNA-mediated knockdown of G3BP1. At step 212, disrupting G3BP1's function in an assembly of axonal stress granule structures may increase intra-axonal protein synthesis and accelerate peripheral nervous system axon regeneration. At step 214, preventing stress granule-like aggregation of axonal proteins during regeneration may increase the rate of axon regrowth.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A prophylactic method for accelerating nerve recovery treating nerve injury in a mammal comprising:
introducing a polypeptide, wherein the polypeptide is amino acid sequence SEQ ID NO: 2, comprising between 15 and 20 amino acids to increase axon growth in neurons or accelerating nerve regeneration at a nerve injury site in the mammal; and
wherein the polypeptide interferes with function of stress granules and increases intra-axonal rates of translation of proteins needed for nerve regeneration.

2. The method of claim 1, wherein the polypeptide specifically targets mRNA storage sites in neurons and increases rates of neuron regeneration.

3. The method of claim 1, wherein the polypeptide disrupts G3BP functions.

4. The method of claim 3, wherein disruption of G3BP functions:
activates intra-axonal mRNA translation;
increases axon growth in neurons; and
accelerates nerve regeneration in vivo.

5. The method of claim 3, wherein disruption of G3BP functions is accomplished via transfection of siRNA to promote siRNA-mediated knockdown of G3BP1.

6. The method of claim 5, wherein disrupting G3BP1's function in an assembly of axonal stress granule structures increases intra-axonal protein synthesis and accelerates peripheral nervous system axon regeneration.

7. The method of claim 6, wherein accelerated axon growth regeneration is facilitated by sequestering Imp61 mRNA from translation.

8. A method of increasing axon growth in neurons or accelerating nerve regeneration disrupting G3BP functions comprising:
overexpressing a dominant-negative protein, wherein the protein is introduced by a transporter molecule;
wherein the dominant-negative protein:
disassembles axonal stress granule-like structures
activates intra-axonal mRNA translation;
increases axon growth in neurons; and
accelerates nerve regeneration in vivo; and
wherein the protein is amino acid sequence SEQ ID NO: 2.

9. The method of claim 8, wherein the protein is cell permeable and targets mRNA storage sites in neurons.

10. The method of claim 8, wherein preventing stress granule-like aggregation of axonal proteins during regeneration increases the rate of axon regrowth.

* * * * *